United States Patent
Schilling et al.

(10) Patent No.: US 10,576,290 B2
(45) Date of Patent: Mar. 3, 2020

(54) FACILITATING TELEMETRY DATA COMMUNICATION SECURITY BETWEEN AN IMPLANTABLE DEVICE AND AN EXTERNAL DEVICE

(71) Applicant: Medtronic, Inc., Minneapolis, MN (US)

(72) Inventors: Eric A. Schilling, Ham Lake, MN (US); Christopher T. House, Pine Island, MN (US); Gary P. Kivi, Maple Grove, MN (US); Karen J. Kleckner, Blaine, MN (US); John W. Komp, Brooklyn Park, MN (US); Nicholas C. Wine, Minneapolis, MN (US); Matthew R. Yoder, Crystal, MN (US); Bo Zhang, Blaine, MN (US)

(73) Assignee: Medtronic, Inc., Minneapolis, MN (US)

(*) Notice: Subject to any disclaimer, the term of this patent is extended or adjusted under 35 U.S.C. 154(b) by 197 days.

(21) Appl. No.: 15/220,667

(22) Filed: Jul. 27, 2016

(65) Prior Publication Data
US 2018/0028827 A1 Feb. 1, 2018

(51) Int. Cl.
A61N 1/372 (2006.01)
G08C 17/02 (2006.01)
A61N 1/00 (2006.01)
H04Q 9/00 (2006.01)

(52) U.S. Cl.
CPC ........... *A61N 1/37252* (2013.01); *A61N 1/00* (2013.01); *A61N 1/37217* (2013.01); *A61N 1/37223* (2013.01); *A61N 1/37254* (2017.08);
*A61N 1/37264* (2013.01); *G08C 17/02* (2013.01); *H04Q 9/00* (2013.01); *G08C 2201/61* (2013.01);
(Continued)

(58) Field of Classification Search
CPC ............ A61N 1/37252; A61N 1/37217; A61N 1/37223; A61N 1/37264
USPC .......................................... 607/60
See application file for complete search history.

(56) References Cited

U.S. PATENT DOCUMENTS

| 7,155,290 B2 | 12/2006 | Von Arx et al. |
| 7,565,197 B2 | 7/2009 | Haubrich et al. |
| 7,668,596 B2 | 2/2010 | Von Arx et al. |

(Continued)

*Primary Examiner* — Carl H Layno
*Assistant Examiner* — Erin M Piateski

(57) ABSTRACT

Systems, apparatus, methods and non-transitory computer readable media facilitating telemetry data communication security between an implantable device and an external clinician device are provided. An implantable device can include a security component configured to generate security information based on reception of a clinician telemetry session request from the clinician device via a first telemetry communication protocol. The security information can include a session identifier and a first session key, and the clinician telemetry session request can include a clinician device identifier associated with the clinician device. The implantable device can further include a communication component configured to establish a clinician telemetry session with the clinician device using a second telemetry communication protocol based on determining that a connection request, received via the second telemetry communication protocol, was transmitted by the clinician device based on inclusion of the clinician device in the connection request.

32 Claims, 12 Drawing Sheets

(52) U.S. Cl.
CPC ..... *G08C 2201/93* (2013.01); *H04Q 2209/43* (2013.01); *H04Q 2209/86* (2013.01)

(56) References Cited

U.S. PATENT DOCUMENTS

| | | | |
|---|---|---|---|
| 7,831,828 B2 | 11/2010 | Von Arx et al. | |
| 8,145,320 B2 | 3/2012 | Corndorf et al. | |
| 8,281,408 B2 | 10/2012 | Corndorf | |
| 8,594,801 B2 | 11/2013 | Corndorf et al. | |
| 8,682,437 B2 | 3/2014 | Kalpin et al. | |
| 8,706,251 B2 | 4/2014 | Von Arx et al. | |
| 8,868,201 B2 | 10/2014 | Roberts et al. | |
| 8,897,344 B2 | 11/2014 | Maguire | |
| 9,687,658 B2 | 6/2017 | Wu et al. | |
| 9,855,433 B2 | 1/2018 | Shahandeh et al. | |
| 2004/0260363 A1* | 12/2004 | Von Arx et al. ... | A61N 1/37252 607/60 |
| 2009/0182395 A1* | 7/2009 | Blaha ................ | A61N 1/37223 607/60 |
| 2011/0202113 A1 | 8/2011 | Persson et al. | |
| 2012/0108922 A1 | 5/2012 | Schell et al. | |
| 2012/0172690 A1 | 7/2012 | Anderson et al. | |
| 2012/0172941 A1 | 7/2012 | Rys | |
| 2012/0271380 A1* | 10/2012 | Roberts et al. .... | A61N 1/37252 607/60 |
| 2013/0214909 A1 | 8/2013 | Meijers et al. | |
| 2014/0188348 A1 | 7/2014 | Gautama et al. | |
| 2014/0214104 A1 | 7/2014 | Greenhut et al. | |
| 2014/0273824 A1* | 9/2014 | Fenner et al. ....... | H04B 5/0031 455/41.1 |
| 2014/0330327 A1 | 11/2014 | Thompson-Nauman et al. | |
| 2015/0065047 A1 | 3/2015 | Wu et al. | |
| 2015/0133951 A1 | 5/2015 | Seifert et al. | |
| 2015/0148868 A1 | 5/2015 | Shahandeh et al. | |
| 2015/0341785 A1* | 11/2015 | Young et al. ......... | H04W 12/04 607/60 |
| 2016/0330573 A1* | 11/2016 | Masoud et al. ......... | H04W 4/90 |
| 2016/0374124 A1* | 12/2016 | Gothe et al. ....... | A61N 1/37264 |
| 2017/0026777 A1 | 1/2017 | Denboer et al. | |

* cited by examiner

US 10,576,290 B2

FACILITATING TELEMETRY DATA COMMUNICATION SECURITY BETWEEN AN IMPLANTABLE DEVICE AND AN EXTERNAL DEVICE

TECHNICAL FIELD

This disclosure relates generally to implantable devices and, more particularly, to systems, apparatus, methods and computer-readable storage media facilitating telemetry data communication security between an implantable device and an external device.

BACKGROUND

Implantable medical devices (IMDs) are often utilized in modern healthcare to facilitate the ability for patients to lead healthy and full lives. For example, IMDs such as pacemakers, implantable cardioverter-defibrillators (ICDs), neurostimulators, and drug pumps can facilitate management of a wide range of ailments, including, but not limited to, cardiac arrhythmias, diabetes, and Parkinson's disease. Patients and medical care providers can monitor the IMD and assess a patient's current and historical physiological state to identify conditions or predict impending events.

The sophistication of IMDs is evolving to provide for advanced computing and telemetry capabilities. There is a desire to use commercially available or non-proprietary telemetry communication protocols for wireless communication between implantable devices and external devices in order to more easily facilitate widespread provisioning of telemetry solutions. However, as commercially available telemetry protocols are employed to perform telemetry with an implantable device, the knowledge of how to initiate and conduct a telemetry session with the implantable device can become publicly available. As a result, it is important that the implantable device securely provide or receive sensitive information to or from only authorized devices. Accordingly, systems, methods, apparatus and computer-readable storage media that facilitate telemetry data communication security between an implantable device and an external device are desired.

SUMMARY

The following presents a simplified summary of one or more of the embodiments in order to provide a basic understanding of one or more of the embodiments. This summary is not an extensive overview of the embodiments described herein. It is intended to neither identify key or critical elements of the embodiments nor delineate any scope of embodiments or the claims. Its sole purpose is to present some concepts of the embodiments in a simplified form as a prelude to the more detailed description that is presented later. It will also be appreciated that the detailed description can include additional or alternative embodiments beyond those described in the Summary section.

Embodiments described herein include systems, apparatus, methods and computer-readable storage media that facilitate telemetry data communication security between an implantable device and an external device. In some embodiments, the implantable device is or includes an IMD. In other embodiments, the implantable device is or includes a device configured to interact with the IMD. In these embodiments, both the implantable device and the IMD can be implanted within or be coupled to a patient.

In one embodiment, an implantable device is provided. The implantable device includes a housing configured to be implanted at least partially within a patient. The implantable device also includes a memory, coupled to the housing, that stores executable components, and circuitry, coupled to the housing, and configured to at least one of obtain sensed physiological data associated with the patient or deliver a therapy to the patient. The implantable device also includes a processor coupled to the housing that executes the executable components stored in the memory. The executable components can include at least a security component configured to generate security information based on reception of a clinician telemetry session request from a clinician device via a first telemetry communication protocol. The clinician telemetry session request can include a clinician device identifier associated with the clinician device, and the security information can include a unique session identifier and one or more unique session keys. The executable components can further include a communication component configured to activate telemetry communication by the implantable device via a second telemetry communication protocol based on sending the security information to the clinician device using the first telemetry communication protocol. The communication component can further establish a clinician telemetry session with the clinician device using the second telemetry communication protocol based on determining that a connection request, received via the second telemetry communication protocol, was transmitted by the clinician device based on inclusion of the clinician device in the connection request.

In one implementation, the first telemetry communication protocol includes a proprietary telemetry communication protocol and the second telemetry communication protocol comprises a non-proprietary telemetry communication protocol. For example, the first telemetry communication protocol can include a short-range (e.g., induction-based) telemetry communication protocol and the second telemetry communication protocol can include a long-range (e.g., radio frequency (RF)-based) telemetry communication protocol.

In various implementations, in association with activation of telemetry communication by the implantable device using the second telemetry communication protocol, the communication component can be configured to transmit one or more advertisement data packets including the session identifier using the second telemetry communication protocol. The communication component can further receive the connection request based on reception of at least one advertisement data packet of the one or more advertisement data packets by the clinician device and recognition, by the clinician device, of the session identifier in the at least one advertisement data packet.

In some implementations, the one or more unique session keys can include a first session key and the communication component can be configured to encrypt first transmitted data transmitted by the implantable device and decrypt first received data received by the implantable device using the first session key in association with performance of the clinician telemetry session with the clinician device. The security information can also include a second session key and the communication component can be further configured to encrypt second transmitted data transmitted by the implantable device and decrypt second received data received by the implantable device using the second session key or both the second session key and the first session key in association with the performance of the clinician telemetry session with the clinician device.

The security component can also be configured to render the security information unusable to establish or to conduct the clinician telemetry session or another telemetry session between the implantable device and the clinician device or another device at a later time. For example, the security component can remove the security information from memory of the implantable device or render the security information expired. Accordingly, in order for the clinician device or another clinician device to establish and conduct a new telemetry session with the implantable device, the clinician device or the other clinician device and the implantable device can establish and exchange new security information in association with a new clinician session request. Thus, after one set of security information is cleared, a new set of security information can be created via a new session initiation request. The security component can render the security information unusable based on closure of the clinician telemetry session or failure of the implantable device to re-establish the clinician telemetry session with the clinician device using the security information within a defined period of time after loss of the clinician telemetry session.

Another embodiment is directed to a method of ensuring telemetry data communication security between an implantable device and a clinician device. The method can include generating security information, by an implantable device including a processor, based on receiving a clinician telemetry session request from a clinician device via a first telemetry communication protocol. The security information can include a session identifier and a first session key and wherein the clinician telemetry session request can include a clinician device identifier associated with the clinician device. The method can further include sending, by the implantable device, the security information to the clinician device using the first telemetry communication protocol, and establishing, by the implantable device, a clinician telemetry session with the clinician device using a second telemetry communication protocol based on determining that a connection request, received via the second telemetry communication protocol, was transmitted by the clinician device based on inclusion of the clinician device in the connection request. In one implementation, the first telemetry communication protocol includes an induction-based telemetry communication protocol and the second telemetry communication protocol includes a BLUETOOTH® low energy (BLE) based telemetry communication protocol.

In various implementations, the method further includes initiating, by the implantable device, data communication using the second telemetry communication protocol based on the sending the security information to the clinician device, including, transmitting, by the implantable device, one or more advertisement data packets comprising the session identifier using the second telemetry communication protocol. The implantable device can further receive, the connection request based on reception of at least one advertisement data packet of the one or more advertisement data packets by the clinician device and recognition, by the clinician device, of the session identifier in the at least one advertisement data packet. In some implementations, the method further includes employing, by the implantable device, the security information to conduct the clinician telemetry session with the clinician device, and rendering, by the implantable device, the security information unusable to establish or conduct another telemetry session between the implantable device and the clinician device or another device at a later time based on closing of the clinician telemetry session. For example, the security component can remove the security information from memory of the implantable device or render the security information expired. Accordingly, in order for the clinician device or another clinician device to establish and conduct a new telemetry session with the implantable device, the clinician device or the other clinician device and the implantable device can establish and exchange new security information in association with a new clinician session request.

In another embodiment, a system is provided. The system includes an implantable device and a clinician device configured to perform telemetry communication with other devices using a first telemetry communication protocol and a second telemetry communication protocol. The implantable device can include a first telemetry component configured to perform the first telemetry communication protocol, a second telemetry component configured to perform the second telemetry communication protocol, and a security component configured to generate security information based on reception of a clinician telemetry session request from the clinician device via the first telemetry communication component. The security information can include a session identifier and one or more session keys, and the clinician telemetry session request can include a clinician device identifier associated with the clinician device. The second telemetry component can be configured to establish a clinician telemetry session with the clinician device using the second telemetry communication protocol based on determining that a connection request, received via the second telemetry communication protocol, was transmitted by the clinician device based on recognition of the clinician device identifier in the connection request. In one or more implementations, the first telemetry communication protocol facilitates first wireless data communication over a first distance and the second telemetry communication protocol facilitates second wireless data communication over a second distance longer than the first distance.

In various implementations, prior to establishing the clinician telemetry session with the clinician device, the implantable device is further configured to transmit the security information to the clinician device using the first telemetry component, and transmit one or more advertisement data packets including the session identifier using the second telemetry component. The implantable device can further receive the connection request using the second telemetry component based on reception of at least one advertisement data packet of the one or more advertisement data packets by the clinician device and recognition, by the clinician device, of the session identifier in the at least one advertisement data packet. The clinician device can be configured to transmit the connection request using the second telemetry communication protocol based on determining that an advertisement data packet received by the clinician device via the second telemetry communication protocol was transmitted by the implantable device based on inclusion of the session identifier in the advertisement data packet. In some implementations, the implantable device can forgo, using the security component, the telemetry communication and other telemetry communication by the implantable device with a device other than the clinician device using the second telemetry communication protocol during establishment of the clinician telemetry session between the implantable device and the clinician device.

Still in yet another embodiment, a non-transitory computer readable medium is provided. The non-transitory computer readable medium includes computer executable instructions that, in response to execution, cause an implantable device including at least one processor to perform various operations. These operations can include, generating, based on receiving a clinician telemetry session request from a clinician device via a first telemetry communication protocol, security information including a session identifier and one or more session keys, wherein the clinician telemetry session request includes a clinician device identifier associated with the clinician device. These operations can further include sending the security information to the clinician device using the first telemetry communication protocol, transmitting one or more advertisement data packets comprising the session identifier and using a second telemetry communication protocol, and establishing a clinician telemetry session with the clinician device using the second telemetry communication protocol based in part on reception, by the clinician device, of at least one advertisement data packet of the one or more advertisement data packets. In one or more implementations, the operations can further include receiving a connection request from the clinician device via the second telemetry communication protocol, wherein the establishing comprises establishing the clinician telemetry session based on inclusion of the clinician device identifier in the connection request.

Another embodiment is directed to a method performed by a clinician device. The method can include sending, by a clinician device including a processor, a clinician telemetry session request to an implantable device via a first telemetry communication protocol, the clinician telemetry session request including a clinician device identifier and security information including a unique session identifier and one or more session keys. The method can further include transitioning, by the clinician device, from operating using the first telemetry communication protocol to operating using a second telemetry communication protocol based on the sending the clinician telemetry session request, and sending, by the clinician device, a connection request to the implantable device using the second telemetry communication protocol based on receiving, via the second telemetry communication protocol, an advertisement data packet including the unique session identifier, wherein the connection request includes the clinician device identifier. The method can further include performing, by the clinician device, a clinician telemetry session with the implantable device using the one or more session keys based on acceptance of the connection request by the implantable device based on inclusion of the clinician device identifier in the connection request.

Other embodiments and various non-limiting examples, scenarios and implementations are described in more detail below. The following description and the drawings set forth certain illustrative embodiments of the specification. These embodiments are indicative, however, of but a few of the various ways in which the principles of the specification can be employed. Other advantages and novel features of the embodiments described will become apparent from the following detailed description of the specification when considered in conjunction with the drawings.

DETAILED DESCRIPTION OF DRAWINGS

The following detailed description is merely illustrative and is not intended to limit embodiments and/or application or uses of embodiments. Furthermore, there is no intention to be bound by any expressed or implied information presented in the preceding Technical Field, Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Additionally, the following description refers to components being "connected" and/or "coupled" to one another. As used herein, unless expressly stated otherwise, the terms "connected" and/or "coupled" mean that one component is directly or indirectly connected to another component, mechanically, electrically, wirelessly, inductively or otherwise. Thus, although the figures may depict example arrangements of components, additional and/or intervening components may be present in one or more embodiments.

The subject disclosure describes systems, apparatus, methods and computer-readable storage media that facilitate telemetry data communication security between an implantable device and an external device. In various embodiments, systems, apparatus, methods and computer-readable storage media are provided that provide substantial improvements in the field of implantable medical device telemetry security. In particular, the subject systems, apparatus, methods and computer-readable storage media facilitate enhanced security associated with establishing and performing a telemetry session with the implantable device using a non-proprietary RF-based telemetry communication protocol that enables rapid bi-directional telemetry communication with the implantable device of data (e.g., programming data or waveform data associated with a remote clinician telemetry session).

Figure 1:
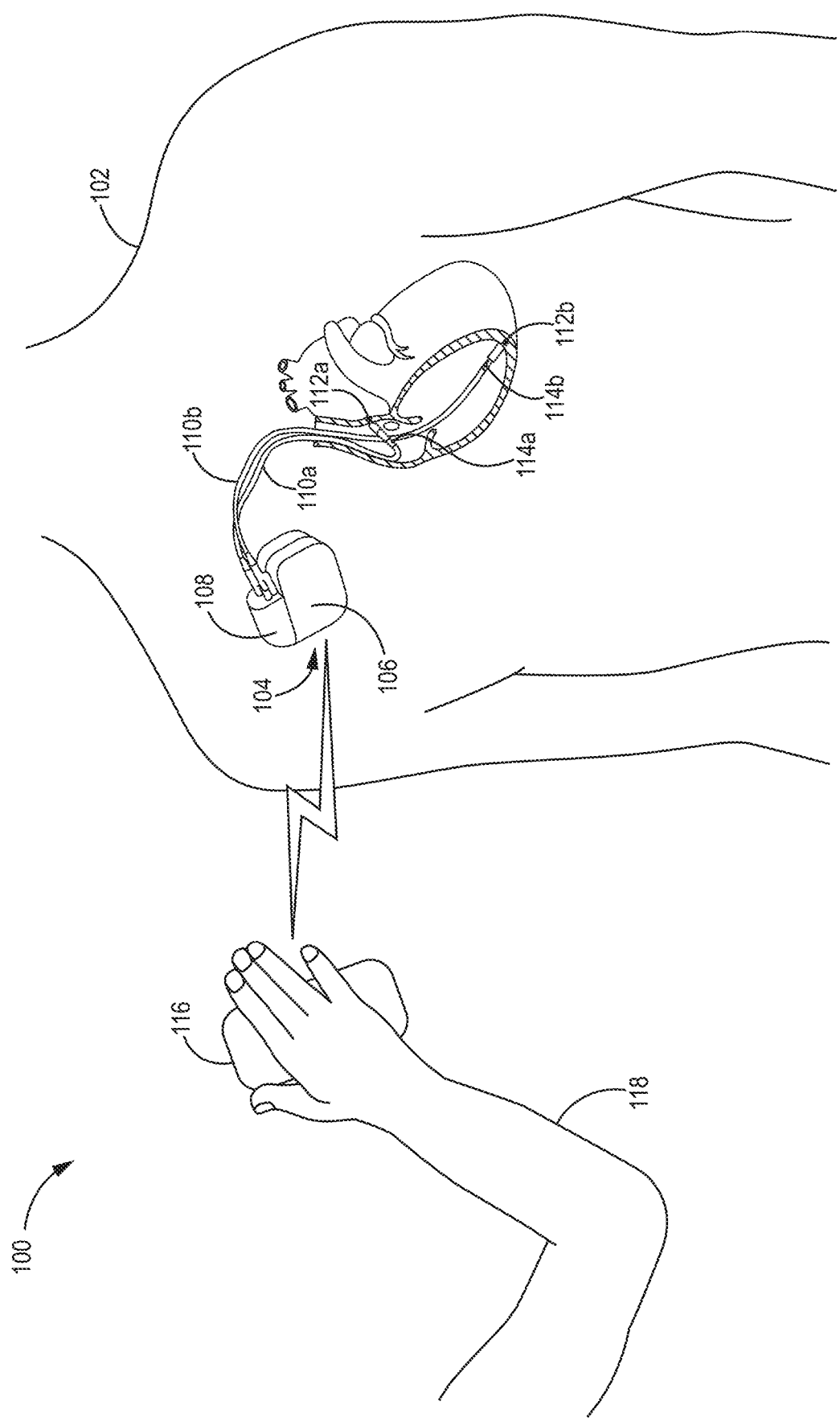
FIG. 1 illustrates a schematic diagram of an example, non-limiting medical device telemetry system configured to facilitate telemetry data communication security between an implantable device and an external device in accordance with one or more embodiments described herein.

With reference now to the drawings, FIG. 1 illustrates a schematic diagram of an example, non-limiting medical device telemetry system 100 configured to facilitate telemetry data communication security between an implantable device and an external device in accordance with one or more embodiments described herein. In the embodiment shown, medical device telemetry system 100 includes an implantable device 104 implanted within a body 102 of a patient and a clinician device 116 external to the body 102 of the patient. The clinician device 116 is shown being held and operated by a clinician 118 (e.g., a doctor, caregiver, a nurse, a technician, etc.) of the patient. In other implementations, the clinician device 116 can be provided on a fixed mount, held by a robotic arm, or the like. The clinician device 116 can also be operated by a remote user or entity using a remote device (not shown) communicatively coupled to the clinician device 116 via a network (e.g., the Internet, an intranet, etc.). In some embodiments, the implantable device 104 is an IMD that can also be configured to facilitate one or more diagnostic or treatment functions relative to the body 102 of a patient. In some embodiments, the implantable device 104 is separate from an IMD that is also implanted within the body 102 and communicatively and/or electrically coupled to the IMD.

Embodiments of devices, apparatus and systems herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

The implantable device 104 can be configured to perform telemetry communication with a variety of external device types, including, but not limited to, a tablet computer associated with a patient or a clinician, a smartphone associated with a patient or a clinician, a medical device associated with a patient or a clinician, an electronic device at a home of a patient or at an office of a clinician, an off-the-shelf device purchased at a store, etc. One or more embodiments of medical device telemetry system 100 are described in connection with facilitating telemetry data communication security between the implantable device 104 and one or more external devices (e.g., clinician device 116), and more particularly, to facilitating heightened security associated with data communication between the implantable device 104 and clinician device 116 in association with performance of a clinician telemetry session. The term "clinician telemetry session" is used herein to refer to a defined type of authorized data communication between the implantable device 104 and an external device that is associated with heightened sensitivity relative to other types of authorized data communication between the implantable device 104 and an external device. For example, a clinician telemetry session can involve transmission of programming data from the external device to the implantable device 104, transmission of sensitive personal information associated with a patient having the implantable device 104 from the implantable device 104 to the external device, or the performance of high power consuming data communication between the implantable device 104 and the external device.

The term "clinician device" is used herein to refer to an external device (e.g., clinician device 116) that is authorized to establish and perform a clinician telemetry session with the implantable device 104. In an exemplary embodiment, the clinician device 116 includes a device that is configured for operation by a clinician 118 of the patient in an in-office or in-person setting in association with performance of a clinician telemetry session with the implantable device 104. However, it should be appreciated that the clinician device 116 can be configured to communicate various types of data with the implantable device 104 (and vice versa) in various contexts and using various telemetry communication techniques.

The type of information communicated between the implantable device 104 and an external device (such as clinician device 116 and other external devices) can vary. For example, using wireless telemetry, the implantable device 104 can transmit information to an external device. The information can include, but is not limited to, sensed physiological or biometric data from the body 102, diagnostic determinations made based on the sensed physiological or biometric data, therapy data associated with a therapy delivered to the body and/or performance data regarding operation and performance of the implantable device 104 (e.g., power level information, information regarding strengths of signals received, information regarding frequency of received interrogation requests, remaining battery life, etc.). In some implementations, the implantable device 104 is an IMD configured to sense the physiological data or the biometric data from the body 102. The IMD can also provide therapy to the body 102 and retain the therapy information regarding the therapy that was provided. In other implementations, the implantable device 104 is associated with an IMD configured to sense the physiological or biometric data or provide the therapy to the body 102. In another example, an external device can employ telemetry communication to read data captured by the implantable device 104. For instance, the clinician device 116 can read electrogram data captured by the implantable device 104 or other physiological or biometric data sensed by the implantable device 104. In another example, using wireless telemetry, an external device (e.g., clinician device 116) can send information or signals to the implantable device 104 to program the implantable device 104 or to configure or re-configure the implantable device 104.

The nature, purpose and type of information communicated between the implantable device 104 and an external device can vary depending on the particular external device with which the implantable device is communicating. For example, the implantable device 104 can be configured to communicate different types of information with different types of external devices, such as a clinician device (e.g., clinician device 116) and a device configured to perform remote monitoring functions associated with the implantable device 104, which is referred to herein as a "monitoring device." The different types of information can be associated with different levels of sensitivity or invasiveness and different amounts of power consumption by the implantable device 104. For example, data communication between the implantable device 104 and a monitoring device can be more restrictive (e.g., read only) than data communication between the implantable device 104 and a clinician device (e.g., read and program). In another example, live or real-time data transmission by the implantable device 104, which is associated with high power consumption by the implantable device 104, can be enabled for performance between the implantable device 104 and a clinician device and disabled for performance between the implantable device104 and a monitoring device.

As used herein, telemetry data communication between the implantable device 104 and a monitoring device (not shown) is referred to as a "monitoring telemetry session." For example, a monitoring telemetry session can be employed between the implantable device 104 and a monitoring device to communicate data captured and/or monitored by the implantable device 104 over the lifetime of the implantable device 104 to a monitoring device that is near the implantable device 104 (e.g., within a few feet or within the same room). For example, the implantable device 104 can be configured to capture (periodically, randomly or otherwise) physiological information about the body 102 and transmit the physiological information to a monitoring device (not shown). The monitoring device can include a device associated with the patient having the implantable device, such as smartphone or a tablet, that is carried by the patient or otherwise located within wireless transmission range of the implantable device on a regular basis (e.g., throughout the day, while the patient is home, while the patient is sleeping, etc.). The implantable device 104 can be configured to establish a monitoring telemetry session periodically and/or based on one or more conditions (e.g., once a day, a few times a day, once an hour, in response to detection of specific triggering physiological information, etc.). Telemetry communication between the implantable device 104 and the monitoring device during a monitoring telemetry session can substantially involve one-way communications transmitted from the implantable device 104 to the monitoring device. In many implementations, telemetry communication during a monitoring telemetry session involves little or no reception of programming or configuration or re-configuration information by the implantable device 104 from the monitoring device.

The information received by the monitoring device from the implantable device 104 can facilitate monitoring the health of the patient over time. In some embodiments, the information can be processed by the monitoring device. In other embodiments, the information received by the monitoring device can be relayed to a server device (not shown) for processing and monitoring the health of the patient. Further, in some embodiments, a server device can provide security measures to establish and perform a monitoring session between a monitoring device and an implantable device 104. For example, the server device can be associated with a patient healthcare monitoring system and network that provides the monitoring device and the implantable device 104 with the authorization and authentication information for establishing a monitoring session. In some implementations, the server device can facilitate paring a monitoring device with an implantable device 104 using the authorization and authentication information in association with performance of monitoring sessions there between.

On the contrary, in various embodiments, the implantable device 104 and the clinician device 116 can be configured to perform a clinician telemetry session that involves a greater amount of data exchange, as well as the exchange of on-demand or real-time data or data considered sensitive or invasive relative to that associated with a remote monitoring telemetry session or another type of telemetry session. In one or more implementations, the clinician telemetry session can facilitate rapid one-way or two-way communication between the implantable device 104 and the clinician device 116. For example, a clinician telemetry session can be initiated by a clinician 118 (e.g., a doctor, a nurse, a medical technician, a caregiver, a mother, etc.) authorized to care for the patient implanted with the implantable device 104 using the clinician device 116. The clinician telemetry session can be employed during interaction between the patient and the patient's clinician 118, such as during scheduled office visits, during routine check-ups, or during emergency situations. Using the clinician device 116, the clinician 118 can employ a clinician telemetry session with the implantable device 104 to program or re-program an operating parameter of the implantable device 104, command the implantable device 104 to apply a therapy to the body 102, send the clinician device 116 specific data captured by the implantable device 104 in real-time, send the clinician device 116 specific data associated with the implantable device 104 that is only authorized for clinician use, and the like. In addition, unlike a monitoring telemetry session wherein the implantable device 104 can be paired with a monitoring device based on security information provided to the respective devices by a remote server device, in many embodiments, the server device may not enable pairing between an implantable device 104 and a clinician device 116 in association with establishing a clinician telemetry session. Accordingly, additional security mechanisms can be employed to ensure a clinician telemetry session is authorized in response to a clinician device 116 attempting to establish a clinician session with an implantable device 104.

Given the different levels of sensitivity of information communicated between the implantable device 104 and the clinician device 116 relative to information communicated between the implantable device and other devices (e.g., a monitoring device or another external device), the implantable device 104 and the clinician device 116 can employ a more robust security mechanism for ensuring or increasing the likelihood that only an authorized clinician device can establish a clinician telemetry session with the implantable device 104. In various embodiments, the implantable device 104 and the clinician device 116 are configured to employ at least two different types of telemetry communication protocols to facilitate the higher level security associated with establishing and performing a clinician telemetry session relative to a level of security associated with establishing and performing a different type of telemetry communication, such as a monitoring telemetry session. In particular, the implantable device 104 and the clinician device 116 can be configured to employ a first telemetry communication protocol to exchange device identification information and security information required for establishing and performing a clinician telemetry session using a second telemetry communication protocol.

In one more embodiments, at least one of the telemetry communication protocols employed by the implantable device 104 and the clinician device 116 includes a proprietary or non-proprietary radio frequency (RF)-based communication protocol. By way of example, but not limitation, the RF-based communication protocol can include, but is not limited to, BLUETOOTH®, BLE, near field communication (NFC), Wireless Fidelity (Wi-Fi) protocol, ZIGBEE®, RF4CE, WirelessHART, 6LoWPAN, Z-Wave, ANT, and the like.

The implantable device 104 and the clinician device 116 can also communicate using proprietary or non-proprietary communication protocols that involve non-RF-based wireless communication protocols. For example, in one or more embodiments, the implantable device 104 and the clinician device 116 are configured to communicate using an electromagnetic induction-based wireless communication technology. Inductive telemetry uses the mutual inductance established between two closely-placed coils. This type of telemetry is referred to as "inductive telemetry" or "near-field telemetry" because the coils must typically be closely situated for obtaining inductively coupled communication. An example inductive wireless communication technology utilizes an inductive coil in a first device (e.g., the clinician device 116) which, if energized by an external voltage source, produces an inductive field that can be used to transmit communications signals and/or charging signals to a second device (e.g., the implantable device 104). The proximity typically involved with using the inductive telemetry technology can provide enhanced security and allow active IMDs to transmit data and accept data from a device external to the body of the patient. In other embodiments, the implantable device 104, the clinician device 116 and/or the remote can employ infrared (IR)-based communication technologies, ultrasonic based communication technologies, or microwave based communication technologies.

In accordance with one or more embodiments, the first telemetry communication protocol employed by the implantable device 104 and the clinician device 116 to exchange the device identification information and the security information employed for establishing and conducting a clinician telemetry session can be associated with a higher level of security relative to the second telemetry communication protocol employed to establish and conduct the clinician telemetry session can include a non-proprietary telemetry communication protocol. For example, in some implementations the first telemetry communication protocol can include a proprietary telemetry communication protocol, and the second telemetry communication protocol can include a non-proprietary telemetry communication protocol. In another example, the first telemetry communication protocol can limit wireless data communication to a shorter distance (e.g., less than three meters) relative to the distance associated with data communication via the second telemetry communication protocol (e.g., less than 100 meters). As a result, the implantable device 104 and the clinician device 116 would typically need to be closer to one another in order to communicate using the first telemetry communication protocol relative to the distance between the implantable device 104 and the clinician device 116 if communicating using the second telemetry communication protocol.

In another embodiment, the first telemetry communication protocol can include a non-RF based telemetry communication protocol and the second telemetry communication protocol can include a RF-based telemetry communication protocol. For example, the first telemetry communication protocol can include an induction-based protocol, an acoustic-based telemetry protocol, or an infra-red-based protocol, and the second telemetry communication protocol can include a BLE protocol, a NFC protocol, a Wi-Fi protocol, etc.

In other embodiments, the first telemetry communication protocol can include a first RF-based telemetry communication protocol and the second telemetry communication protocol can include a second RF-based telemetry communication protocol. For example, the first telemetry communication protocol can include a NFC protocol, and the second telemetry communication protocol can include a BLE protocol. In another example, the first telemetry communication protocol can include a BLUETOOTH®-based protocol involving a first set of defined communication parameters, and the second telemetry communication protocol can include a BLUETOOTH®-based protocol involving a second set of defined communication parameters.

For exemplary purposes, various embodiments of medical device telemetry system 100 and associated apparatuses, methods, and computer-readable mediums described herein are exemplified wherein the implantable device 104 and the clinician device 116 employ an induction-based telemetry communication as the first telemetry communication approach and BLE communication as a second telemetry communication approach. There is a desire to use commercially available or non-proprietary telemetry communication protocols such as BLE for wireless communication between implantable devices and external devices (e.g., implantable device 104 and clinician device 116) to more easily facilitate widespread provisioning of telemetry solutions. For example, many modern mobile devices such as smartphones, tablets, personal computers (PCs) and the like are configured to communicate using various publicly available telemetry protocols. However, as commercially available telemetry protocols (e.g., BLE) are employed to perform telemetry with an implantable device, the knowledge of how to initiate and conduct a telemetry session with the implantable device can become publicly available. For example, in an embodiment in which BLE is employed by the implantable device 104 to perform telemetry, an unauthorized device may detect an advertisement signal transmitted by the implantable device and attempt to establish a telemetry session with the implantable device. Accordingly, a robust security mechanism that ensures the implantable device 104 establishes and conducts a clinician telemetry session with only an authorized clinician device is of increased importance when the implantable device 104 employs a non-proprietary telemetry communication protocol (e.g., BLE) to perform telemetry communication.

In various embodiments, the establishment of a clinician telemetry session between the implantable device 104 and the clinician device 116 involves a primary telemetry communication exchange between the implantable device 104 and the clinician device using the first telemetry communication protocol (e.g., induction-based) followed by a secondary telemetry communication exchanged between the implantable device 104 and the clinician device 116 using the second telemetry communication protocol (e.g., BLE). In one or more implementations, the primary telemetry communication exchange can begin with a clinician session initiation request sent by the clinician device 116 to the implantable device 104 using the first telemetry communication protocol (e.g., induction). The implantable device 104 can be configured to interpret a clinician session initiation request received from a clinician device (e.g., clinician device 116) via the first telemetry communication protocol as a request to establish a clinician telemetry session with the implantable device 104 using the second telemetry communication protocol.

The primary telemetry communication exchange can involve the exchange of time-sensitive security information and device identification information employed by the implantable device 104 and the clinician device 116 to establish and conduct the requested clinician telemetry session using the second telemetry communication protocol. In one or more embodiments, at least a portion of the time-sensitive security information can be generated by the implantable device 104 based on reception of the clinician session initiation request from the clinician device 116 via the first telemetry communication protocol. In other embodiments, at least a portion of the time-sensitive security information can be provided by the clinician device 116 to the implantable device 104 with the clinician session initiation request via the first telemetry communication protocol. The security information can be regarded as time-sensitive if security information is employed to establish and conduct a currently requested clinician telemetry session between the implantable device and the clinician device that provided the clinician session initiation request using the first telemetry communication protocol. For example, after the currently requested clinician telemetry session is established between the implantable device 104 and the clinician device 116 using the security information is closed, the implantable device 104 can be configured to clear the security information from memory, delete the security information, or otherwise render the security information as expired or unusable in a later telemetry communication session between the implantable device 104 and the clinician device 116 or another external device (not shown). In addition, if the implantable device 104 and the clinician device 116 fail to establish the requested clinician telemetry session using the security information within a defined window of time (e.g., the advertisement period) following transmission of the clinician session initiation request by the clinician device 116 or reception of the clinician session initiation request by the implantable device 104, the implantable device 104 can be configured to clear the security information from memory (e.g., deletes or otherwise treats as expired or unusable). As a result, in order for the same clinician device (e.g., clinician device 116) or a new clinician device to establish a new clinician telemetry session with the implantable device 104, in some embodiments, the methodology described herein can require the clinician device 116 or the new clinician device to send a new clinician session initiation request to the implantable device 104 using the first telemetry communication protocol, thus prompting the implantable device 104 to generate new security information to be employed for establishing and conducting the new clinician telemetry session.

In one or more implementations, the time-sensitive security information includes an identifier for the clinician device 116, a unique session identifier, and one or more unique session encryption keys. The identifier for the clinician device 116 can include a radio frequency module (RFM) address of the RF communication components, a media access control (MAC) address, a universal unique identifier (UUID), or another unique value, symbol or character combination that identifies the clinician device 116. The session identifier can include a dynamically generated unique identifier that is associated with the implantable device 104 and the currently requested clinician session. The time-sensitive security information can also include one or more unique session keys. The one or more unique session keys can be employed by the implantable device 104 and the clinician device 116 to encrypt and decrypt information communicated between the respective devices during the clinician telemetry session. In one implementation, the one or more unique session keys includes a unique link layer encryption key (e.g., a 128 bit link layer encryption key). In another implementation, the one or more unique session keys can include a unique application layer encryption key (e.g., a 128 bit application layer encryption key). Still in other implementations, the one or more unique session keys can include a third encryption key, a fourth encryption key, etc. In some implementations, the implantable device 104 and the clinician device 116 can be configured to employ specific keys or combinations of different keys to encrypt and decrypt defined types of data in association with performance of the clinician telemetry session. For example, the implantable device 104 and the clinician device 116 can be configured to encrypt and/or decrypt a first type of data using the link layer encryption key and the application layer key, and encrypt and/or decrypt a second type of data (e.g., waveform data) using only the link layer encryption key.

In various embodiments, the implantable device 104 can be configured to generate the security information based in part on reception of the clinician session initiation request from the clinician device 116 via the first telemetry communication protocol. For example, based on reception of the clinician session initiation request, the implantable device 104 can be configured to generate a unique session identifier, such as a UUID including random numbers, or another unique identifier. In one or more embodiments, the identifier for the clinician device 116 for establishment of the requested clinician telemetry session with the implantable device 104 is included in the clinician session initiation request sent by the clinician device 116 to the implantable device 104. For example, the clinician session initiation request can include a RFM address associated with the clinician device, a MAC address associated with the clinician device 116, or another unique identifier for the clinician device 116. The implantable device 104 can also be configured to generate the one or more unique session keys based on reception of the clinician session initiation request from the clinician device 116.

According to these embodiments, in association with the primary data exchange using the first telemetry communication protocol, the implantable device 104 can be further configured to send the dynamically generated time-sensitive security information to the clinician device 116 using the first telemetry communication protocol. For example, in an embodiment in which the first telemetry communication protocol includes an induction-based protocol, the implantable device 104 can be configured to transmit the security information (e.g., the dynamically generated unique session identifier and the one or more unique session keys) to the clinician device 116 using an induction-based telemetry communication signal.

In various additional embodiments, the clinician device 116 can be configured to send the security information to the implantable device 104 using the first telemetry communication protocol in association with the clinician session initiation request. For example, in some implementations, the clinician device 116 can generate a unique session identifier and one or more unique session keys. In other implementations, another device (e.g., a remote server device (not shown)) can provide the clinician device 116 with the unique session identifier and the one or more unique session keys based on a request for the security information provided by the clinician device 116 to the other device. The clinician device 116 can also include the unique session identifier and the one or more session keys along with the clinician device identifier in the clinician session initiation request.

Still in other embodiments, a portion of the security information employed to establish and conduct a requested clinician telemetry session can be provided by the clinician device 116 and another portion of the security information can be provided by the implantable device 104. For example, the clinician device 116 can be configured to generate a unique session identifier and include the unique session identifier in a clinician session initiation request along with the clinician device identifier. The clinician device can send the clinician session initiation request to the implantable device 104 using the first telemetry communication protocol. Based on reception of the clinician session initiation request, the implantable device 104 can generate the one or more unique session keys and send the one or more unique session keys back to the clinician device 116 using the first telemetry communication protocol.

By employing a first telemetry communication protocol to exchange the security information employed to establish a clinician telemetry session that is considered more secure than the second telemetry communication protocol employed to conduct the clinician telemetry session, the ability for a non-authorized external device to establish and conduct a clinician telemetry session with the implantable device 104 is significantly impeded. For example, when the first telemetry communication protocol includes a proprietary telemetry communication protocol, in some embodiments, only those external devices configured to operate using the proprietary telemetry communication protocol will be able to establish and conduct a clinician telemetry session with the implantable device. In another example, when the first telemetry communication protocol includes an induction-based telemetry communication protocol, the inherent proximity for the external device to be located relative to the implantable device 104 (e.g., less than one meter) to use the inductive telemetry protocol provides an enhanced level of security. In addition, because the implantable device 104 and/or the clinician device 116 can be configured to generate the security information employed to establish and conduct a requested clinician telemetry session (e.g., the unique identifier for the implantable device 104 and the one or more unique encryption keys) in association with a clinician session initiation request provided by the requesting clinician device (e.g., clinician device 116), the security information is not previously known or available to either device, including the implantable device 104 and the requesting clinician device. The security information can be time-sensitive and limited for usage to establish and conduct only the currently requested clinician telemetry session. Thus the ability for a non-authorized external device to inadvertently or maliciously receive the security information employed to establish and perform a clinician telemetry session with the implantable device 104 is significantly minimized Based on the implantable device 104 and the clinician device 116 having exchanged the identification information and the security information using the first telemetry communication protocol (e.g., the primary telemetry communication exchange), in one or more embodiments, the implantable device 104 and the clinician device 116 can perform the secondary telemetry communication exchange using the second telemetry communication protocol. As noted above, the secondary telemetry communication exchange can involve establishing the clinician telemetry session between the implantable device 104 and the clinician device 116 using the second telemetry communication protocol and the device identification information and the security information provided during the primary telemetry communication exchange.

In one or more embodiments, the implantable device 104 can be configured to initiate telemetry communication by the implantable device using the second telemetry communication protocol (e.g., BLE) based on transmission of the security information (e.g., the unique session identifier and the one or more unique session keys) to the clinician device 116 via the first telemetry communication protocol. For example, the implantable device 104 can activate one or more RF components of the implantable device 104 (e.g., an RF transmitter, an RF receiver, or an RF transceiver) in accordance with a defined RF telemetry communication protocol employed by the implantable device 104. Likewise, the clinician device 116 can be configured to initiate telemetry communication by the clinician device 116 using the second telemetry communication protocol based on reception of the security information from the implantable device 104 via the first telemetry communication protocol. In other embodiments in which the clinician device 116 includes the security information with the clinician session initiation request, the implantable device 104 can activate telemetry communication using the second telemetry communication protocol based on reception of the clinician session initiation request. The clinician device 116 can activate telemetry communication using the second telemetry communication protocol based on transmission of the clinician session initiation request.

In various implementations, in association with initiation of telemetry communication by the implantable device 104 using the second telemetry communication protocol, the implantable device 104 can begin advertising in accordance with defined parameters for the second telemetry communication protocol (e.g., BLE). The term "advertising," as used herein, can refer to the transmission of advertisement data packets or signals that include information indicating the implantable device 104 is ready or available to communicate with an external device (e.g., clinician device 116). The information can indicate the implantable device 104 is ready or available to communicate with an external device using the second telemetry communication protocol (e.g., BLE). In some embodiments, an external device (e.g., clinician device 116) actively employing the second telemetry communication protocol can receive advertisement signals transmitted by the implantable device 104. Reception of an advertisement signal by an external device from the implantable device is referred to herein as a "discovery event."

The number, frequency and/or timing of advertisement data packets to be transmitted by the implantable device 104 while advertising in association with the secondary telemetry communication exchange can be defined in the second telemetry communication protocol. In one or more embodiments, the implantable device 104 can be configured to transmit N advertisement data packets every M milliseconds (ms) for a defined advertisement period of P minutes. For example, the implantable device 104 can be configured to transmit three advertisement data packets every 80 ms for an advertisement period of five minutes or until a connection is established, whichever occurs first. In one or more implementations, the implantable device 104 can be configured to include the unique session identifier (e.g., the implantable device 104 unique UUID) in the one or more advertisement data packets transmitted by the implantable device 104. In some implementations, the implantable device 104 can also be configured to encrypt the information included in the one or more advertisement data packets using an encryption key generated by the implantable device 104 in association with the primary telemetry communication exchange. For example, the implantable device 104 can be configured to generate a link layer encryption key and employ the link layer encryption key to encrypt the information included in the one or more advertisement data packets.

Based on the clinician device 116 initiating telemetry communication by the clinician device 116 using the second telemetry communication protocol (e.g., BLE), the clinician device 116 can scan for advertisement data packets transmitted by the implantable device 104. For example, in one or more embodiments, the clinician device 116 can be configured to accept only advertisement data packets that include the unique identifier for the implantable device 104 that was provided by the implantable device 104 to the clinician device 116 in association with the primary telemetry communication exchange. The clinician device 116 can ignore detected or received advertisement data packets from other external devices that do not include the unique session identifier.

In various implementations, based on reception of an advertisement data packet including the unique session identifier, the clinician device 116 can generate and send a connection request back to the implantable device 104 using the second telemetry communication protocol. In an embodiment in which the advertisement data packet is encrypted by the implantable device 104 using a unique encryption key (e.g., a link layer encryption key), the clinician device 116 can also decrypt the one or more advertisement data packets received from the implantable device 104 using the unique session key encryption key (e.g., which was provided by the implantable device 104 to the clinician device 116 during the primary telemetry communication exchange). The connection request can include information that requests establishment of the clinician telemetry session with the implantable device 104 and the unique identifier for the clinician device 116 (e.g., an RFM address associated with the clinician device 116 that was provided by the clinician device 116 to the implantable device 104 in association with the primary telemetry communication exchange). In one or more embodiments, the clinician device 116 can be configured to encrypt the connection request with a unique encryption key (e.g., the link layer encryption key) received from the implantable device 104 in association with the primary telemetry communication exchange.

The implantable device 104 can establish the requested clinician telemetry session with the clinician device 116 based on reception and decryption (if applicable) of the connection request and recognition of the unique identifier for the clinician device 116 included in the connection request (e.g., which was provided by the clinician device 116 to the implantable device 104 in association with the primary telemetry communication exchange). For example, based on reception of a properly formatted (which can involve inclusion of the clinician device identifier), and/or properly encrypted, connection request from the clinician device 116, the implantable device 104 can accept the connection request. The implantable device 104 can also send the clinician device 116 an acceptance message indicating the connection request has been accepted. If this acceptance message is received by the clinician device 116, the clinician session can be considered as established and the clinician device 116 and the implantable device 104 can begin performing data communication in accordance with defined parameters for the clinician session. In one or more embodiments in which the implantable device 104 is performing the subject secondary telemetry communication exchange, the implantable device 104 can ignore any incoming data packets (e.g., connection requests) from external devices other than those including the unique identifier for the clinician device 116 (e.g., the clinician device RFM address, the clinician device MAC address or the like). In various implementations, while the clinician telemetry session is established between the implantable device 104 and the clinician device 116, the implantable device 104 and the clinician device 116 are configured to forgo establishment of another telemetry session with another external device using the second telemetry communication protocol.

In one or more embodiments, the implantable device 104 can restrict the duration of time after which the implantable device 104 begins advertising (e.g., the advertisement period) for establishment of the clinician telemetry session. For example, the implantable device 104 may not receive a properly formatted/encrypted connection request from the clinician device 116 within the advertisement period, thereby causing the advertisement period to expire. In another example, the implantable device 104 may receive a properly formatted/encrypted connection request from the clinician device 116 within the advertisement period yet be unable to respond to the connection request with an acceptance message or otherwise establish the clinician telemetry session with the clinician device 116 due to channel interference, low received signal strength (e.g., based on separation of the implantable device 104 and the specific clinician device beyond wireless transmission range), or another factor. In some implementations, the advertisement period associated with the secondary telemetry communication exchange is set to five minutes. However, it should be appreciated that the advertisement period can be any suitable length of time that facilitates establishing a clinician telemetry session with an authorized clinician device while limiting an amount of current drain associated with fruitlessly advertising.

Once established, the implantable device 104 and the clinician device 116 can begin conducting or performing the clinician telemetry session. For example, the implantable device 104 can transmit requested data to the clinician device 116 and receive data transmitted by clinician device 116, and vice versa. The type of data communication performed between the implantable device 104 and the clinician device 116 during a clinician telemetry session can vary depending on the features and functionalities of the implantable device 104, the clinician device 116, and the purpose of the clinician telemetry session. In various embodiments, the clinician telemetry session can facilitate dynamic bi-directional (e.g., one-way and two-way) communication between the implantable device 104 and the clinician device 116. For example, the implantable device 104 can receive one or more downlink data packets from the clinician device 116 (e.g., data packets including commands or programming information, etc.), and process uplink data packets for transmission to the clinician device 116 (e.g., data packets including waveform information). In one or more embodiments, the implantable device 104 and the clinician device 116 are configured to encrypt and decrypt some or all data communicated during the clinician telemetry session using the one or more of the session keys generated by the implantable device 104 in association with the primary telemetry communication exchange (e.g., in response to reception of the clinician session initiation request from the clinician device 116 via the first telemetry communication protocol). In some implementations, the implantable device 104 and the clinician device 116 can employ different session keys or combinations of session keys to encrypt and/or decrypt specific types of data. For example, the implantable device 104 can be configured to encrypt live or real-time data transmitted by the implantable device 104 using a first session encryption key and encrypt other data using either a second session encryption key or both the first and second session encryption keys.

In various embodiments, after the clinician session is completed and closed (e.g., via a direct request to close the clinician session provided from the clinician device 116 to the implantable device 104), the implantable device 104 can remove the security information employed for the clinician session from memory or otherwise render the security information unusable in a later telemetry session between the implantable device 104 and an external device (e.g., including the clinician device previously involved in the clinician session). For example, the implantable device 104 can remove the unique session identifier, the one or more unique session keys and the identifier for the clinician device 116. Accordingly, in order for the clinician device 116 or another clinician device to establish and conduct a new telemetry session with the implantable device 104, the clinician device 116 or the other clinician device and the implantable device 104 can establish and exchange new security information in association with a new clinician session request. In some implementations, after the clinician session is closed, the implantable device 104 can operate using a telemetry communication mode that employs the second telemetry communication protocol in a modified manner relative to the manner employed by the implantable device 104 in association with the secondary telemetry communication exchange. For example, the implantable device 104 can operate using the second telemetry communication protocol in a manner that reduces an amount of power consumption by the implantable device 104 relative to the manner in which the implantable device 104 operates using the second telemetry communication protocol in association with the secondary telemetry communication exchange. For instance, if the second telemetry communication protocol involves advertising (e.g., BLE), the implantable device 104 can employ a shorter advertising period (e.g., about one second) relative to the advertising period employed during the secondary telemetry communication exchange. In addition, the implantable device 104 can be configured to advertise according to a low duty cycle (e.g., once every three minutes the implantable device 104 can advertise for one second). On the contrary, in association with the secondary telemetry communication exchange, the implantable device 104 can continually advertise for a defined advertisement period (e.g., five minutes) until the advertisement period expires or a clinician telemetry session is established, whichever occurs first.

In another implementation, after the clinician session is closed, the implantable device 104 can be configured to determine whether enabling and operating using the second telemetry communication protocol is necessary, desired, or safe. For example, if the second telemetry communication protocol includes an RF based telemetry communication protocol, under certain contexts, the operating using the second telemetry communication protocol may be unnecessary, undesired, or unsafe. According to this implementation, if the implantable device 104 determines that operating using the second telemetry communication technology is unnecessary, undesired or unsafe, the implantable device can deactivate or disable telemetry communication by the implantable device 104 using the second telemetry communication protocol.

In some instances, in lieu of the clinician session being intentionally closed, the clinician session can be inadvertently lost. Loss of a clinician session refers to a loss in the integrity of the telemetry connection between the implantable device 104 and the clinician device 116 in association with performance of the clinician session. For example, loss of a clinician session can include an inability to receive or transmit data packets by the implantable device 104 and/or the clinician device 116 in association with performance of the clinician session, or an inability to receive or transmit data packets with a defined level of throughput. Loss of a clinician session can be caused by various factors such as, but not limited to, channel interference, separation of the implantable device 104 and the clinician device 116 beyond wireless transmission range, or another factor. In some embodiments, if the clinician session is lost, the implantable device 104 can provide the clinician device 116 a short period of time to re-establish the clinician session using the current device identification information and security information. For example, the implantable device 104 can begin advertising again in the manner performed by the implantable device 104 in association with the secondary telemetry communication exchange. In this scenario, the implantable device 104 can employ the same advertisement period the implantable device 104 is configured to employ during the secondary telemetry communication exchange (e.g., five minutes) or a shorter advertisement period (e.g., three minutes). If the clinician session is not re-established within the advertisement period, the clinician session can be treated as closed and the implantable device 104 can react in the manner discussed above upon the closing of a clinician session (e.g., the implantable device 104 can remove the security information from memory or otherwise render the security information unusable for establishment of a future clinician telemetry session).

Accordingly, in various implementations, if a clinician session established between the implantable device 104 and the clinician device 116 is lost, the methodologies described herein can be such that the only device capable of re-establishing the clinician session with the implantable device 104 is the clinician device 116. In particular, any other external device will not be able to establish a clinician session with the implantable device 104 because no other external device will have the security information shared between the implantable device 104 and the clinician device 116 in association with the establishment of the clinician session during the primary telemetry communication exchange. In some embodiments, this security information, which can include unique identifiers for both the clinician device 116 and the implantable device 104 and one or more session keys, can be required to establish the lost clinician session. For example, in order to re-establish the lost clinician session, based on reception of a new advertisement data packet transmitted by the implantable device that includes the unique identifier for the implantable device 104, the clinician device 116 can send a new connection request to the implantable device 104 and include the identifier for the clinician device 116 (e.g., a RFM address associated with the clinician device 116) in the new connection request. The implantable device 104 can be configured to only accept a new connection request from the clinician device 116 and thus only accept new connection requests that include the identifier for the clinician device 116.

Further, in various implementations, the implantable device 104 and the clinician device 116 are configured to encrypt and decrypt data packets communicated between one another in association with the clinician session using the one or more unique session keys privy to only the clinician device 116 and the implantable device 104. Accordingly, in some embodiments, no other external device can decrypt data packets received from the implantable device 104 and the implantable device 104 will not be able to decrypt data packets received from an external device other than the clinician device 116. Additional details of example embodiments of the subject telemetry communication security measures associated with establishing a clinician telemetry session are discussed in greater detail infra with respect to FIGS. 2A, 2B, 3A, 3B, 4, 5, 6, 7, 8, 9 and 10.

As noted above, unlike a clinician telemetry session, in various embodiments, the security measures associated with establishing a monitoring telemetry session can be provided by and controlled by a remote system, such as a remote medical device monitoring system that facilitates remotely monitoring patients having implantable devices (e.g., a system associated with managing and ensuring telemetry security of various patients' implanted devices). For example, the remote medical device monitoring system can include a remote server device that facilitates pairing an implantable device 104 with a particular monitoring device by providing the respective devices with defined authentication and authorization information that can be employed to set up and perform a remote monitoring session.

For instance, in one embodiment, prior to implantation or after implantation, the implantable device 104 can receive (e.g., from the remote server device) and store information identifying the one or more external monitoring devices with which the implantable device 104 is authorized to establish a monitoring session, such as unique identifiers for the one or more external monitoring devices. The one or more external monitoring devices, for example, can include a home monitoring device provided to the patient in association with receiving the implantable device 104 or a smartphone or tablet device previously owned and/or operated by the patient and later programmed to facilitate a remote monitoring functionality associated with the patient's implantable device 104. The implantable device 104 can further be configured to establish a monitoring session with only those authorized monitoring devices. For example, the implantable device 104 can be configured to only establish a monitoring session based on receipt of a request for the monitoring session. The request can be received from an authorized monitoring device based on inclusion of the unique identifier for the authorized monitoring device previously provided to the implantable device 104 by the remote server device.

In another embodiment, prior to implantation or after implantation, the implantable device 104 can receive (e.g., from the remote server device) and store information identifying a unique identifier for the implantable device 104 and one or more unique keys to be used by the implantable device 104 for pairing with a monitoring device. Information identifying the unique identifier for the implantable device 104 and the one or more unique keys can be stored at the remote sever device. In order to facilitate paring a monitoring device with the implantable device 104, the remote server device can provide the monitoring device with the unique identifier for the implantable device 104 and the one or more unique keys. The monitoring device can employ this information to pair with the implantable device 104. The monitoring device can also be configured to provide the implantable device 104 with a unique identifier for the monitoring device in association with the initial pairing.

After the implantable device 104 is paired with a monitoring device using the authentication and authorization information provided by the remote medical device monitoring system, the respective devices can establish and perform monitoring sessions with limited security checks. In various embodiments, the implantable device 104 can also employ an RF-based telemetry communication protocol (e.g., BLE) to establish a monitoring session with a monitoring device. For example, the implantable device 104 can activate one or more RF components of the implantable device 104 (e.g., an RF transmitter, an RF receiver, or an RF transceiver) in accordance with a defined RF telemetry communication protocol employed by the implantable device 104 (e.g., BLE). Similar to the mechanism employed by the implantable device 104 to establish a clinician session, the implantable device 104 can also transmit one or more advertisement data packets according to a defined RF telemetry communication protocol (e.g., BLE). In some implementations, the transmission rate of the advertisement packets sent by the implantable device 104 in association with establishing a monitoring session is lower or slower than the transmission rate of the advertisement packets sent by the implantable device 104 in association with establishing a clinician session. For example, the transmission rate associated with establishing a monitoring session may be about one advertisement data packet every three minutes compared to one advertisement data packet every one second for establishing a clinician session. The one or more advertisement data packets transmitted by the implantable device 104 in association with establishing a monitoring session can also include information that uniquely identifies the implantable device 104 (e.g., a unique identifier for the implantable device 104 provided to the implantable device 104 by the remote server device) and indicating the implantable device 104 is ready and available to conduct a monitoring session.

In various embodiments, a monitoring device that is paired with the implantable device 104 can be configured to receive and recognize advertisement data packets sent by the implantable device 104 in association with establishing a monitoring session. For example, a monitoring device that is paired with the implantable device 104 can recognize the unique identifier for the implantable device 104 included in the advertisement packet, wherein the identifier was previously provided to the monitoring device by the remote server device. Based on reception of an advertisement packet and recognition of the unique identifier, the monitoring device can be configured to send a response to the implantable device 104 requesting establishment of a monitoring session. The response can also include information that uniquely identifies the monitoring device, such as a unique identifier for the monitoring device that was previously provided by the monitoring device to the implantable device 104 in association with pairing and/or that was previously provided by the remote server device to the implantable device 104.

The implantable device 104 can further be configured to receive a response to an advertisement data packet transmitted in association with establishing a monitoring session and determine whether the response is received from an authorized monitoring device. For example, based on reception of an advertisement data packet including a unique identifier for the implantable device 104 that is recognized by an authorized monitoring device previously paired with the implantable device 104, the authorized monitoring device can be configured to send a response to the implantable device 104 that requests to establish a monitoring session. The response can also include the unique identifier for the monitoring device that was previously provided to the implantable device 104. The implantable device 104 can further be configured to establish the requested monitoring session based on recognition of the unique identifier for the monitoring device in the response. In one or more embodiments, during the monitoring session, the implantable device 104 can be configured to communicate a defined type of information with the monitoring device. For example, the implantable device 104 can send the monitoring device physiological information that the implantable device 104 previously obtained about the patient. In another example, the implantable device 104 can send the monitoring device operating performance information monitored by the implantable device 104.

Medical device telemetry system 100 can provide several technical solutions to technical drawbacks associated with existing implantable device telemetry systems. In particular, one or more embodiments of medical device telemetry system 100 can provide substantial improvements in the field of implantable device telemetry security in association with usage of a non-proprietary RF-based telemetry communication protocol by an implantable device. One or more embodiments of the non-proprietary telemetry communication protocol (e.g., BLE) can enable rapid (and high power consuming) bi-directional telemetry communication with the implantable device 104 of data considered invasive or sensitive (e.g., programming data or waveform data associated with a remote clinician telemetry session). However, in order to ensure or increase the likelihood that only authorized clinician devices can employ the non-proprietary telemetry communication protocol to perform such clinician telemetry session data communications with the implantable device 104, one or more embodiments of medical device telemetry system 100 can employ an enhanced security mechanism that utilizes another telemetry communication protocol (e.g., induction) to initiate a clinician session with the implantable device 104. In addition, in some embodiments, the security mechanism involves the generation of time-sensitive security information by the implantable device 104 at the time of initiation of the clinician session that can only be employed to establish and conduct the currently requested clinician session. Further, in accordance with the security mechanism, in some embodiments, the implantable device 104 will not generate the security information unless the implantable device 104 receives a properly formatted clinician session initiation request via the other telemetry communication protocol.

It is to be appreciated that the implantable device 104 and the clinician device 116 can include one or more devices, transducers and/or circuits that can facilitate telemetry communication and disablement of telemetry communication in accordance with one or more of the telemetry communication technologies described above. For example, the implantable device 104 and the clinician device 116 can include an RF transmitter that transforms electrical power into a signal associated with transmitted data packets. In some embodiments, the implantable device 104 and the clinician device 116 can include one or more RF devices, transducers and/or circuits that can facilitate receiving information from one another or additional external devices. For example, the implantable device 104 and the clinician device 116 can include an RF receiver that transforms a signal into electrical power. The implantable device 104 and the clinician device 116 can also include hardware, software, or a combination of hardware and software that can facilitate non-RF-based telemetry communication technologies and protocols. For example, the implantable device 104 and the clinician device 116 can include an induction antenna and associated circuitry that can facilitate receiving and interpreting induction-based signals and generating and transmitting induction-based signals.

The clinician device 116 can include any suitable computing device that can be operated by a clinician and configured to communicate with the implantable device 104 using a first (e.g., induction-based, NFC-based, etc.) telemetry communication protocol and a second (e.g., BLE-based) telemetry communication protocol. For example, the clinician device 116 can include a smartphone, a tablet, a dedicated handheld device, a wearable device, or another suitable device. In some embodiments, the clinician device 116 can include an output and/or input device such as a display, a speaker, a microphone, a keypad, a touch screen, etc. In other embodiments, the clinician device 116 can be configured to communicate with another external device to receive input and/or render output.

In various embodiments, the implantable device 104 can include any number of different types of implantable devices configured to communicate with the clinician device 116 or another external device. The particular, size, shape, placement and/or function of the implantable device 104 may not be critical to the subject disclosure in some embodiments. In one embodiment, as mentioned, the implantable device 104 is or includes an IMD. For example, some example IMDs can include, but are not limited to, cardiac pacemakers, cardiac defibrillators, cardiac re-synchronization devices, cardiac monitoring devices, cardiac pressure monitoring devices, spinal stimulation devices, neural stimulation devices, gastric stimulation devices, diabetes pumps, drug delivery devices, and/or any other medical devices. In various embodiments, however, the implantable device 104 can be or include any number of other types of implantable devices that are not IMDs.

For exemplary purposes, the implantable device 104 is illustrated in medical device telemetry system 100 as an IMD implanted within the chest of a patient and configured to provide medical treatment or therapy associated with a heart disease or condition (e.g., an implantable cardioverter-defibrillator (ICD) and/or a pacemaker). In addition to the medical treatment, the implantable device 104 can also be configured to provide the data packetizing and communication operations described herein. The implantable device 104 includes a housing 106 within which electrical components and one or more power sources are housed. The electrical components can be powered via the one or more power sources. A power source (not shown) can include, but is not limited to, a battery, a capacitor, a charge pump, a mechanically derived power source (e.g., microelectromechanical systems (MEMs) device), or an induction component.

The electrical components can vary depending on the particular features and functionality of the implantable device 104. In various embodiments, these electrical component can include, but are not limited to, one or more processors, memories, transmitters, receivers, transceivers, sensors, sensing circuitry, therapy circuitry, antennas and other components. In an embodiment, the electrical components can be formed on or within a substrate that is placed inside the housing 106. The housing 106 can be formed from conductive materials, non-conductive materials or a combination thereof. For example, housing 106 can include a conductive material, such as metal or metal alloy, a non-conductive material such as glass, plastic, ceramic, etc., or a combination of conductive and non-conductive materials. In some embodiments, the housing 106 can be a biocompatible housing (e.g., a liquid crystal polymer, etc.).

In the embodiment shown, the implantable device 104 is also an IMD and further includes leads 110*a,b* connected to the housing 106. The leads 110*a,b* extend into the heart and respectively include one or more electrodes. For example, as depicted in medical device telemetry system 100, leads 110*a,b* each include a respective tip electrodes 112*a,b* and ring electrodes 114*a,b* located near a distal end of their respective leads 110*a,b*. In embodiments in which implanted, tip electrodes 112*a,b* and/or ring electrodes 114*a,b* are placed relative to or in a selected tissue, muscle, nerve or other location within the body 102 of the patient. As depicted in medical device telemetry system 100, tip electrodes 112*a,b* are extendable helically shaped electrodes to facilitate fixation of the distal end of leads 110a,b to the target location within the body 102 of the patient. In this manner, tip electrodes 112a,b are formed to define a fixation mechanism. In other embodiments, one or both of tip electrodes 112a,b may be formed to define fixation mechanisms of other structures. In other instances, leads 110a,b may include a fixation mechanism separate from tip electrodes 112a,b. Fixation mechanisms can be any appropriate type, including a grapple mechanism, a helical or screw mechanism, a drug-coated connection mechanism in which the drug serves to reduce infection and/or swelling of the tissue, or other attachment mechanism.

Leads 110a,b are connected at a proximal end of the implantable device 104 via connector block 108. Connector block 108 may include one or more receptacles that interconnect with one or more connector terminals located on the proximal end of leads 110a,b. Leads 110a,b are ultimately electrically connected to one or more of the electrical components within housing 106. One or more conductors (not shown) extend within leads 110a,b from connector block 108 along the length of the lead to engage the ring electrodes 114a,b and tip electrodes 112a,b, respectively. In this manner, each of tip electrodes 112a,b and ring electrodes 114a,b is electrically coupled to a respective conductor within its associated lead bodies. For example, a first electrical conductor can extend along the length of the body of lead 110a from connector block 108 and electrically couple to tip electrode 112a and a second electrical conductor can extend along the length of the body of lead 110a from connector block 108 and electrically couple to ring electrode 114a. The respective conductors may electrically couple to circuitry, such as a therapy module or a sensing module, of the implantable device 104 via connections in connector block 108. In one or more embodiments, the implantable device 104 can be configured to deliver therapy to the heart (or other location) via the electrical conductors to one or more of electrodes 112a and 112b and 114a and 114b. In the case of pacing therapy, for example, therapy circuitry within the implantable device 104 can generate and deliver pacing pulses via a unipolar electrode configuration, e.g., using electrodes 112a and 112b and a housing electrode of the implantable device 104. In other instances, the therapy circuitry within the implantable device 104 can deliver pacing pulses via a bipolar electrode configuration, e.g., using electrodes 112a and 112b and ring electrodes 114a and 114b. The therapy circuitry may include one or more pulse generators, capacitors, and/or other components capable of generating and/or storing energy to deliver as pacing therapy in accordance with a pacing regime stored within memory.

Implantable device 104 can also receive sensed electrical signals on the electrical conductors from one or more of electrodes 112a, 112b and 114a, 114b. The implantable device 104 can sense the electrical signals using either a unipolar or bipolar electrode configuration. Sensing circuitry of the implantable device 104 may process the sensed electrical signals and the implantable device 104 may analyze the processed and/or or sensed electrical signals and provide the pacing as a function of the sensed electrical signal. The sensing circuitry may include one or more sense amplifiers, filters, rectifiers, threshold detectors, comparators, analog-to-digital converters (ADCs), or other analog or digital components.

The configuration, features and functionality of implantable device 104 are merely provided as an example. In other examples, the implantable device 104 can include more or fewer leads extending from the housing 106. For example, the implantable device 104 can be coupled to three leads, e.g., a third lead implanted within a left ventricle of the heart of the patient. In another example, the implantable device 104 can be coupled to a single lead that is implanted within the ventricle of the heart of the patient. In other embodiments, the lead may be an extravascular lead with the electrodes implanted subcutaneously above the ribcage/sternum or substernally underneath or below the sternum. Example extravascular ICDs having subcutaneous electrodes are described in U.S. Patent Publication No. 2014/0214104 (now U.S. Pat. No. 9,072,914) (Greenhut et al.) and U.S. Patent Publication No. 2015/0133951 (Seifert et al.), each of which is incorporated herein in its entirety. One example extravascular ICD having substernal electrodes is described in U.S. Patent Publication No. 2014/0330327 (Thompson-Nauman et al.). In some embodiments, the implantable device 104 can include other leads (e.g., atrial lead and/or left ventricular lead). As such, implantable device 104 can be used for single chamber or multi-chamber cardiac rhythm management therapy. In addition to more or fewer leads, each of the leads may include more or fewer electrodes. In instances in which the implantable device 104 is used for therapy other than pacing, (e.g., defibrillation or cardioversion), the leads can include elongated electrodes, which may, in some instances take the form of a coil. The therapy circuitry of the implantable device 104 can generate and deliver defibrillation or cardioversion shocks to the heart via any combination of the elongated electrodes and housing electrode. The therapy circuitry may include one or more high voltage (HV) output capacitors and a HV charging circuit, which may include one or more capacitors, resistors, inductors, transformers, switches, or other analog or digital components, and discharging circuitry to deliver cardioversion or defibrillation therapy, including, for example, an H-bridge circuit. In another embodiment, the implantable device 104 can include leads with a plurality of ring electrodes, (e.g., as used in some implantable neurostimulators), without a tip electrode or with one of the ring electrodes functioning as the "tip electrode."

In another embodiment, the implantable device 104 may include no leads, as in the case of an intracardiac pacemaker or a leadless pressure sensor. In the case of an intracardiac pacemaker, the device may include a housing sized to fit wholly within the patient's heart. In one example, the housing may have a volume that is less than 1.5 cc and, more preferably, less than 1.0 cubic centimeter (cc). However, the housing may be greater than or equal to 1.5 cc in other examples. The intracardiac pacemaker includes at least two electrodes spaced apart along the outer portion of the housing for sensing cardiac electrogram signals and/or delivering pacing pulses. Example intracardiac pacemakers are described in commonly-assigned U.S. Patent Publication No. 2012/0172690 (Anderson et al.), U.S. Patent Publication No. 2012/0172941 (now U.S. Pat. No. 8,386,051) (Kenneth), and U.S. Patent Publication No. 2014/0214104 (now U.S. Pat. No. 9,072,914) (Greenhut et al.), each of which is incorporated herein in its entirety. In the case of a leadless pressure sensor, the device can include a housing having a fixation member and a pressure sensing component. One example of a leadless pressure sensor is described in U.S. Patent Publication No. 2012/0108922 (now U.S. Pat. No. 8,475,372) (Schell et al.), which is incorporated herein in its entirety.

Clinician device 116 can include any suitable computing device configured to communicate with implantable device 104. In some embodiments, the clinician device 116 can be a remote electronic device. For example, the clinician device 116 can include, but is not limited to, a handheld computing device, a mobile phone, a smart phone, a tablet personal computer (PC), a laptop computer, a desktop computer, a personal digital assistant (PDA) and/or a wearable device. In some embodiments, the clinician device 116 can include a display that can present information associated with the implantable device 104. In another embodiment, the clinician device 116 can include an application and/or a program associated with the implantable device 104.

Figure 2A:
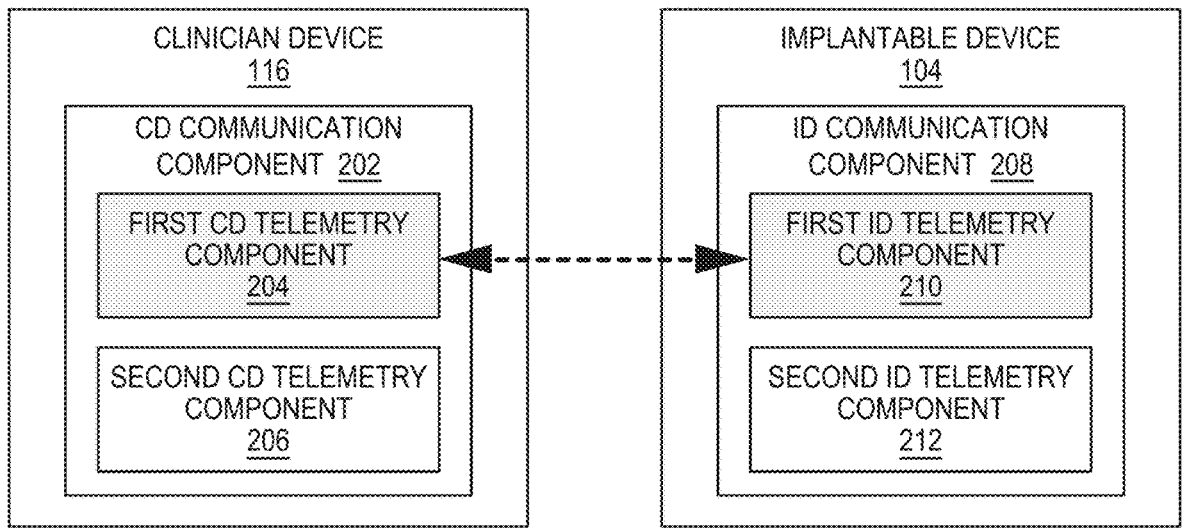
FIG. 2A illustrates an example telemetry communication exchange between an implantable device and a clinician device using a first telemetry communication protocol in accordance with one or more embodiments described herein.
Figure 2B:
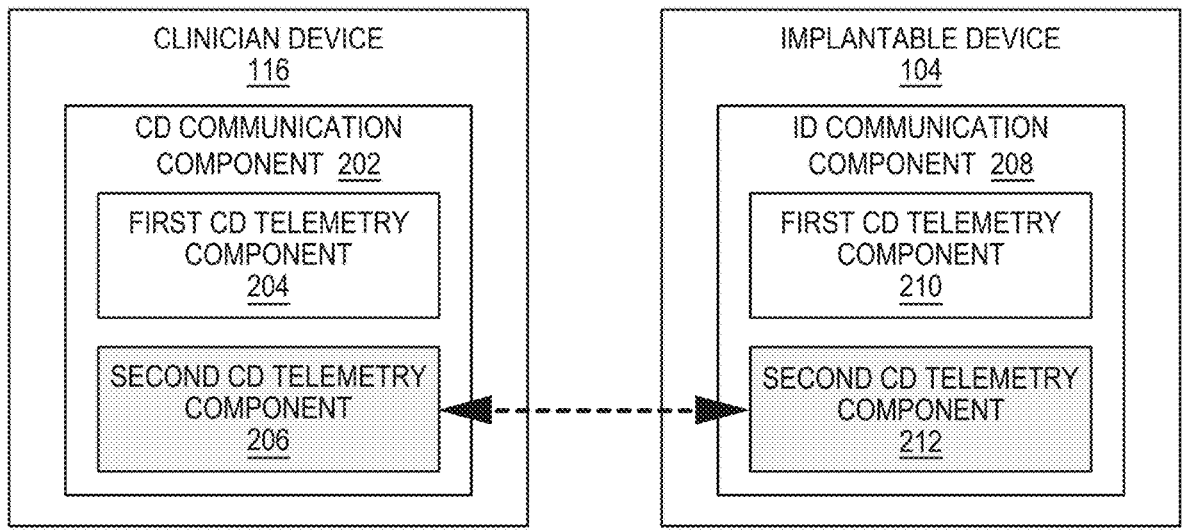
FIG. 2B illustrates another example telemetry communication exchange between an implantable device and a clinician device using a second telemetry communication protocol in accordance with one or more embodiments described herein.

FIGS. 2A and 2B, illustrate different aspects of telemetry communication between an implantable device (e.g., implantable device 104) and a clinician device (e.g., clinician device 116) in association with establishing a secure clinician telemetry session in accordance with one or more embodiments described herein. FIG. 2A illustrates an example primary telemetry communication exchange between implantable device 104 and clinician device 116 using a first telemetry communication protocol in accordance with one or more embodiments described herein. FIG. 2B illustrates an example secondary telemetry communication exchange between implantable device 104 and clinician device 116 using a second telemetry communication protocol in accordance with one or more embodiments described herein. Repetitive description of like elements employed in respective embodiments described herein is omitted for sake of brevity.

In one or more embodiments, the clinician device 116 and the implantable device 104 can respectively include communication components configured to facilitate telemetry communication using at least a first telemetry communication protocol and a second telemetry communication protocol. For example, the clinician device 116 can include clinician device (CD) communication component 202, which can include a first clinician device telemetry component 204 configured to facilitate telemetry communication using a first telemetry communication protocol and a second clinician device telemetry component 206 configured to facilitate telemetry communication using a second telemetry communication protocol. Similarly, the implantable device 104 can include implantable device (ID) communication component 208, which can include a first implantable device telemetry component 210 configured to facilitate telemetry communication using the first telemetry communication protocol and a second implantable device telemetry component 212 configured to facilitate telemetry communication using the second telemetry communication protocol.

In various embodiments, the clinician device communication component 202, the first clinician device telemetry component 204, and second clinician device telemetry component 206 can provide the same or similar features and functionalities as the corresponding components of the implantable device 104: the implantable device communication component 208, the first implantable device telemetry component 210 and the second implantable device telemetry component 212, respectively. Accordingly, in some embodiments, the description of the features and functionalities of the clinician device communication component 202, the first clinician device telemetry component 204, and second clinician device telemetry component 206 are applicable to the implantable device communication component 208, the first implantable device telemetry component 210 and the second implantable device telemetry component 212, respectively (and vice versa).

The clinician device communication component 202 and the implantable device communication component 208 can facilitate telemetry communication between the clinician device 116 and the implantable device 104 using one or more networks (not shown) and/or wired or wireless communication protocols. In some implementations, the clinician device communication component 202 can also facilitate communication between the clinician device 116 and one or more other external devices (in addition to the implantable device 104) using a variety of networks (not shown) and/or wired or wireless communication protocols. Likewise, the implantable device communication component 208 can facilitate telemetry communication between the implantable device 104 and one or more other external devices (e.g., in addition to the clinician device 116) using a variety of networks (not shown) and/or wired or wireless communication protocols. For example, in one or more embodiments, the clinician device communication component 202 and the implantable device communication component 208 can communicate with one another or other devices using NFC, or another type of communication protocol over a PAN or a LAN, (e.g., a Wi-Fi network) that can provide communication over greater distances than distances for the NFC protocol or that can accomplish one or more aspects described herein (such as increased security).

In some embodiments, the clinician device communication component 202 and the implantable device communication component 208 can control transmission and reception of one or more data packets via a communication channel associated with a communication protocol utilizing lower energy consumption than a conventional communication protocol for wirelessly transmitting data. For example, in a non-limiting example, the clinician device communication component 202 and the implantable device communication component 208 can control transmission and reception of data packets using the BLE protocol. Other communication protocols that can be employed by the clinician device communication component 202 and the implantable device communication component 208 can include, but are not limited to, other BLUETOOTH® communication protocols, a Session Initiation Protocol (SIP) based protocol, a ZIGBEE® protocol, a RF4CE protocol, a WirelessHART protocol, a 6LoWPAN (IPv6 over Low power Wireless Personal Area Networks) protocol, a Z-Wave protocol, an ANT protocol, an ultra-wideband (UWB) standard protocol, an RF communication protocol, and/or other proprietary and non-proprietary communication protocols.

In one or more embodiments, the first clinician device telemetry component 204 and the first implantable device telemetry component 210 can include hardware, software, or a combination of hardware and software configured to facilitate telemetry communication using a first telemetry communication protocol (e.g., a transmitter, receiver, antenna, processor or other components employed to carry out telemetry communication using the first telemetry communication protocol). In addition, the second clinician device telemetry component 206 and the second implantable device telemetry component 212 can include hardware, software, or a combination of hardware and software employed to facilitate telemetry communication using a second telemetry communication protocol (e.g., a transmitter, receiver, antenna, processor or other components employed to carry out telemetry communication using the second telemetry communication protocol).

As described supra, the first telemetry communication protocol can include a telemetry communication protocol that is considered more secure than the secondary telemetry communication protocol. For example, the first telemetry communication protocol can be associated with a shorter wireless transmission range relative to the wireless transmission range of the second telemetry communication protocol. According to this example, the first telemetry communication protocol can facilitate telemetry communication between devices separated by about one meter or less while the second telemetry communication protocol can facilitate telemetry communication between devices separated by greater than one meter, and more typically over a range of about three to twenty meters. In another example the first telemetry communication protocol can include a proprietary telemetry communication protocol and the second telemetry communication protocol can include a non-proprietary telemetry communication protocol.

In one or more embodiments, the first telemetry communication protocol includes a non-RF-based telemetry communication protocol, such as a magnetic induction-based telemetry communication protocol, and the second telemetry communication protocol includes a near-field RF-based telemetry communication/technology, such as BLE or the like. According to these embodiments, the first clinician device telemetry component 204 and the first implantable device telemetry component 210 can respectively include an induction antenna or coil and repeater configured to generate and receive electromagnetic induction signals in association with the primary telemetry communication exchange between the clinician device 116 and the implantable device 104. For example, an induction antenna or coil and repeater associated with the first clinician device telemetry component 204 can generate and transmit an induction signal that corresponds to a clinician session initiation request and includes information identifying the clinician device 116 (e.g., an RFM address of the clinician device 116). In some embodiments, the clinician session initiation request can also include a portion or all of the unique security information (e.g., a unique session identifier and/or one or more unique session keys) employed to establish and conduct the clinician session. An induction antenna or coil and repeater associated with the first implantable device telemetry component 210 can receive and interpret the clinician session initiation request induction signal. The induction antenna or coil and repeater associated with the first implantable device telemetry component 210 can also generate and send an electromagnetic induction signal to the external clinician device that provides a response to the clinician session initiation request. For example, in some embodiments, the response can include all or a portion of the unique security information generated by the implantable device 104 (e.g., a UUID and one or more unique session keys).

Likewise, the second clinician device telemetry component 206 and the second implantable device telemetry component 212 can respectively include one or more RF components configured to generate, receive, and interpret RF signals using a BLE protocol. For example, the second clinician device telemetry component 206 and the second implantable device telemetry component 212 can control operation of an RF transceiver and RF repeater of the clinician device 116 and the implantable device 104, respectively, and control transmission and reception of one or more RF data packets by the clinician device 116 and the implantable device 104 in association with performance of BLE telemetry communication between the respective devices (e.g., during performance of the secondary telemetry communication exchange and the clinician session). In some embodiments, as an alternative or in addition to including a transceiver, the second clinician device telemetry component 206 and the second implantable device telemetry component 212 can include a transmitter and a receiver that do not share common circuitry.

In some implementations, the second clinician device telemetry component 206 and the second implantable device telemetry component 212 can include or be associated with existing RF modules or components of the clinician device 116 and the implantable device 104, respectively. For example, the clinician device 116 and/or the implantable device 104 can include RF modules or components that are employed by the respective devices to perform telemetry communications that are not associated with performance of a clinician session between the clinician device 116 and the implantable device 104. For instance, the clinician device 116 can include a computing device (e.g., a tablet, a smartphone, etc.), that has been configured to perform clinician device applications in addition to various other unrelated computing applications. According to these embodiments, the second clinician device telemetry component 206 and the second implantable device telemetry component 212 can respectively include software configured to control operation of the existing RF modules or components of the clinician device 116 and the implantable device 104, respectively, to perform defined BLE operations associated with establishing and performing a clinician session. The second clinician device telemetry component 206 and the second implantable device telemetry component 212 can also receive information uniquely identifying the existing RF modules or components of the respective devices (e.g., RFM addresses) prior to performance of the operations associated with establishing and performing a clinician session (e.g., in association with configuring of the respective devices to have clinician session applications).

As shown in FIG. 2A, the clinician device 116 and the implantable device 104 can respectively activate and employ the first clinician device telemetry component 204 and the first implantable device telemetry component 210 in association with performance of the primary telemetry communication exchange. For example, during the primary telemetry communication exchange, the clinician device 116 can activate and employ the first clinician device telemetry component 204 to generate and send a clinician session initiation request message to the implantable device 104 (e.g., via a first electromagnetic induction signal). The implantable device 104 can activate and employ the first implantable device telemetry component 210 to receive and interpret the clinician session initiation signal and to generate and send a response message to the clinician session initiation signal (e.g., via a second electromagnetic induction signal). For example, the response message can include all or a portion of the unique security information (e.g., the unique session identifier and one or more unique session keys) generated by the implantable device 104 based on reception of the clinician session initiation request. The clinician device 116 can further interpret the received response message via the first clinician device telemetry component 204.

As shown in FIG. 2B, the clinician device 116 and the implantable device 104 can respectively activate and employ the second clinician device telemetry component 206 and the second implantable device telemetry component 212 in association with performance of the secondary telemetry communication exchange. For example, based on reception of the clinician session response message or transmission of a clinician session initiation request including the security information, the clinician device 116 can direct the clinician device communication component 202 to transition from communicating with the implantable device 104 using the first clinician device telemetry component 204 to using the second clinician device telemetry component 206. According to this example, using the second clinician device telemetry component 206, the clinician device 116 can detect one or more advertisement data packets transmitted by the implantable device 104. Similarly, based on transmission of the clinician session response message or based on reception of a clinician session initiation request including the security information, the implantable device 104 can direct the implantable device communication component 208 to begin transmitting the one or more advertisement data packets including the unique session identifier using the second implantable device telemetry component 212.

In addition, based on reception of one or more of the advertisement data packets by the second clinician device telemetry component 206, the clinician device 116 can activate and employ the second clinician device telemetry component 206 to generate and send a connection request to the implantable device 104 and to receive a connection request acceptance message from the implantable device 104. Likewise, the implantable device 104 can activate and employ the second implantable device telemetry component 212 to receive the connection request and generate and send the connection request acceptance message to the clinician device 116 (e.g., based on a determination that the connection request was provided by the clinician device 116 based on inclusion of the clinician device identifier in the connection request and/or based on an ability of the implantable device 104 to decrypt the connection request using one or more of the unique session keys).

Figure 3A:
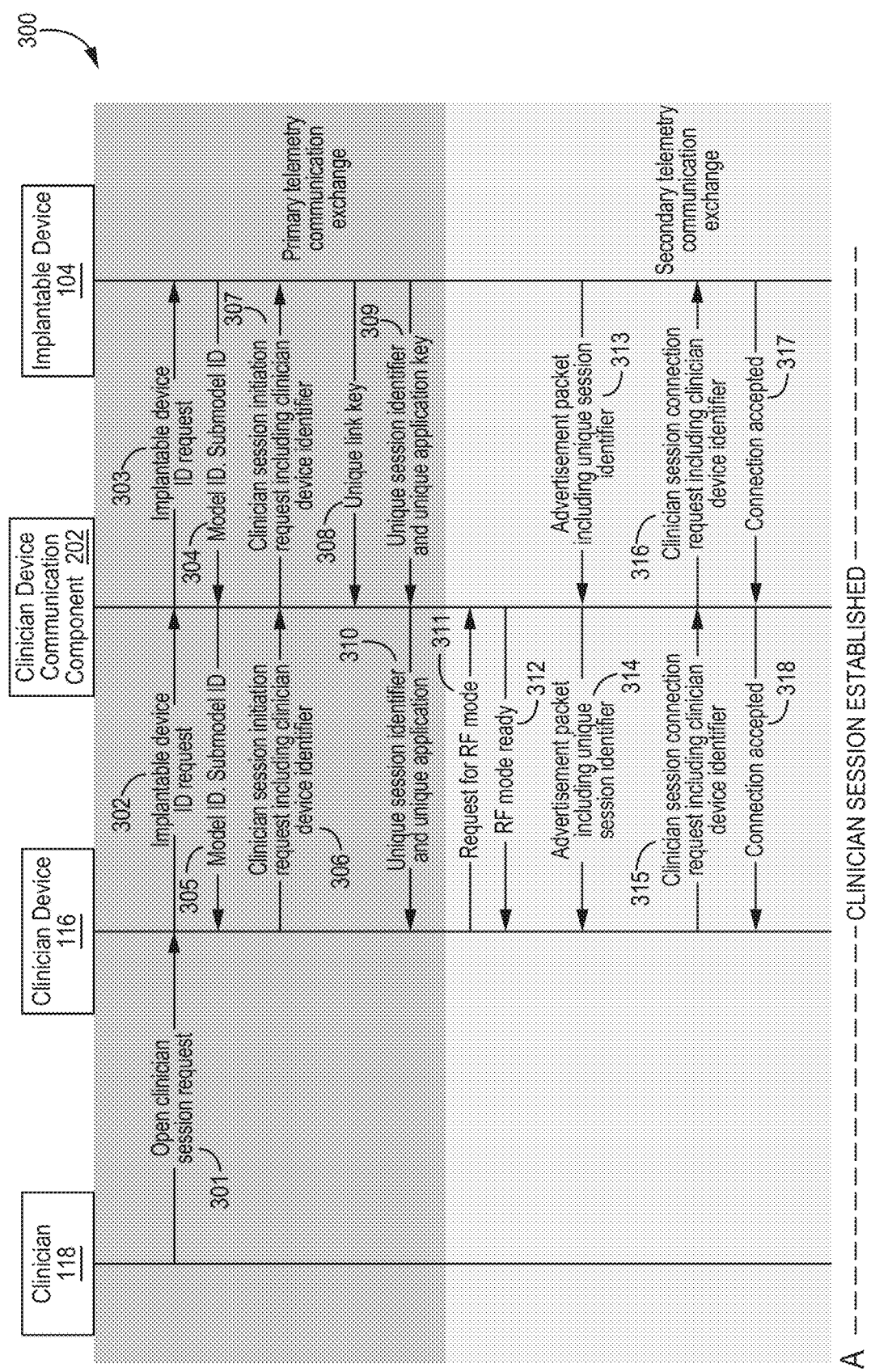
FIG. 3A illustrates a non-limiting signaling diagram of a method facilitating establishment of a secure clinician telemetry session between an implantable device and a clinician device in accordance with one or more embodiments described herein.

FIG. 3A illustrates a non-limiting signaling diagram of a signaling method 300 facilitating establishment of a secure clinician telemetry session between an implantable device (e.g., implantable device 104) and a clinician device (e.g., clinician device 116) in accordance with one or more embodiments described herein. Repetitive description of like elements employed in other embodiments described herein is omitted for sake of brevity.

With reference to FIGS. 1, 2A, 2B and 3A, signaling method 300 includes a flow of signaling commands or messages that can be communicated between the clinician 118, the clinician device 116, the clinician device communication component 202, and the implantable device 104 in association with establishing a clinician session in accordance with one or more embodiments described herein. In the embodiment shown, the clinician device communication component 202 is separated from the clinician device 116 to indicate that the clinician device communication component 202 includes one or more hardware components associated with telemetry communication by the clinician device 116 that may not be dedicated to the clinician session functionality of the clinician device 116. For example, the clinician device communication component 202 can include an RF module employed by the clinician device 116 when operating in capacities other than a clinician device (e.g., a cellular phone, a personal computing device, etc.). In this embodiment, the clinician device communication component 202 can include magnetic induction telemetry hardware components and associated circuitry as well as RF telemetry hardware components and associated circuitry that are included on or within the clinician device 116. At least some of the processing functionality associated with generating and interpreting signals transmitted or received by the clinician device communication component 202 in association with establishing and performing a clinician session can be distributed to one or more dedicated clinician components of the clinician device 116.

At 301, the clinician 118 (e.g., a caregiver or entity that operates the clinician device 116) provides an open session initiation request to the clinician device 116. For example, using a clinician session application provided on the clinician device 116, the clinician 118 can provide input selecting an "open clinician session" feature provided by the application. Based on reception of the open session clinician request, at 302 the clinician device 116 can send the clinician device communication component 202 an implantable device identifier (ID) request, and at 303, the clinician device communication component 202 generates and sends the implantable device ID request to the implantable device 104 using the first telemetry communication protocol (e.g., via the first clinician device telemetry component 204). In one or more implementations of signaling method 300, the first telemetry communication protocol includes an electromagnetic induction-based telemetry communication protocol. This implantable device ID request can be employed to inform the clinician device 116 about the particular implantable device with which the clinician device is about to communicate. In particular, an implantable device implanted within a patient can be associated with a unique ID and submodel ID. The model ID and submodel ID for the implantable device 104 can be associated with information accessible to the clinician device 116 that describes characteristics of the implantable device 104, such as the type of the implantable device 104, the capabilities of the implantable device 104, patient information about the patient implanted with the implantable device 104, etc. At 304, the implantable device 104 can transmit a response to the implantable device ID request using the first telemetry communication protocol and sends the clinician device communication component 202 the model ID and submodel ID for the implantable device 104. At 305, the clinician device communication component 202 can provide the model ID and submodel ID for the implantable device 104 to the clinician device 116.

At 306, the clinician device 116 can provide a clinician session initiation request to the clinician device communication component 202. The clinician session initiation request can include a unique identifier for the clinician device 116 (e.g., the RFM address for the clinician device 116) and can request security information for the clinician session from the implantable device 104. At 307, the clinician device communication component 202 can generate and send the clinician session initiation request to the implantable device 104 using the first telemetry communication protocol. Based on reception of the clinician session initiation request and inclusion of the clinician device identifier in the clinician session initiation request, the implantable device 104 can generate the requested security information. For example, the implantable device 104 can generate a unique session identifier (e.g., a UUID) and one or more unique session keys. In the embodiment shown, the implantable device 104 can generate a unique link key and/or a unique application key.

At 308, the implantable device 104 can provide the unique link key to the clinician device communication component 202 using the first telemetry communication protocol. At 309, the implantable device 104 can provide the unique session identifier and/or the unique application key to the clinician device communication component 202 using the first telemetry communication protocol. At 310, the clinician device communication component 202 can provide the unique session identifier and/or the unique application key to the clinician device 116. At this point, the implantable device 104 and the clinician device 116 have completed the primary telemetry communication exchange and may begin the secondary telemetry communication exchange.

In accordance with the secondary telemetry communication exchange, at 311, the clinician device 116 can provide a request to the clinician device communication component 202 requesting initiation of telemetry communication using the second telemetry communication protocol. In the embodiment shown, the second telemetry communication protocol includes a RF-based telemetry communication protocol (e.g., BLE). Accordingly, the request at 311 can be identified as a request for RF mode operation by the clinician device communication component 202. At 312, the clinician device communication component 202 can transition from operating using the first telemetry communication protocol to operating using the second telemetry communication protocol and inform the clinician device 116 that the clinician device communication component 202 has initiated operation of the implantable device using the RF mode (e.g., BLE) via an RF mode ready message.

Also in accordance with the secondary telemetry communication exchange, the implantable device 104 can begin transmitting one or more advertisement data packets using the second telemetry communication protocol. The one or more advertisement data packets can include the unique session identifier generated by the implantable device 104 in association with the primary telemetry communication exchange. For example, at 313, the implantable device 104 can send an advertisement packet including the unique session identifier to the clinician device communication component 202. At 314, the clinician device communication component 202 can provide the advertisement packet to the clinician device 116.

At 315, based on reception of the advertisement data packet and a determination that the advertisement data packet originated from the implantable device 104 (e.g., based on recognition of the unique session identifier included in the advertisement data packet), the clinician device 116 can provide a clinician session connection request to the clinician device communication component 202. The clinician session connection request can include information requesting establishment of the clinician session between the clinician device 116 and the implantable device 104 and can further include the clinician device identifier. At 316, the clinician device communication component 202 can generate and send the clinician session connection request to the implantable device 104 using the second telemetry communication protocol.

At 317, based on reception of the clinician session connection request and a determination that the clinician session initiation request was provided by the clinician device 116 (e.g., via recognition of the clinician device identifier in the clinician session connection request), the implantable device 104 can generate and send a connection accepted response message to the clinician device communication component 202 using the second telemetry communication protocol. At 318, the clinician device communication component 202 can provide the connection accepted message to the clinician device 116. At this time, based on reception of the connection accepted message by the clinician device 116, the clinician session is established between the implantable device 104 and the clinician device 116, as indicated via dashed line A. In one or more implementations, one or more data communications between the clinician device communication component 202, and the implantable device 104 performed during the secondary telemetry communication exchange (e.g., the one or more advertisement data packets, the clinician session connection request, and/or the connection accepted message) can be encrypted and decrypted using the unique link key generated by the implantable device 104 and shared between the implantable device 104 and clinician device communication component 202 in association with the primary telemetry communication exchange.

Figure 3B:
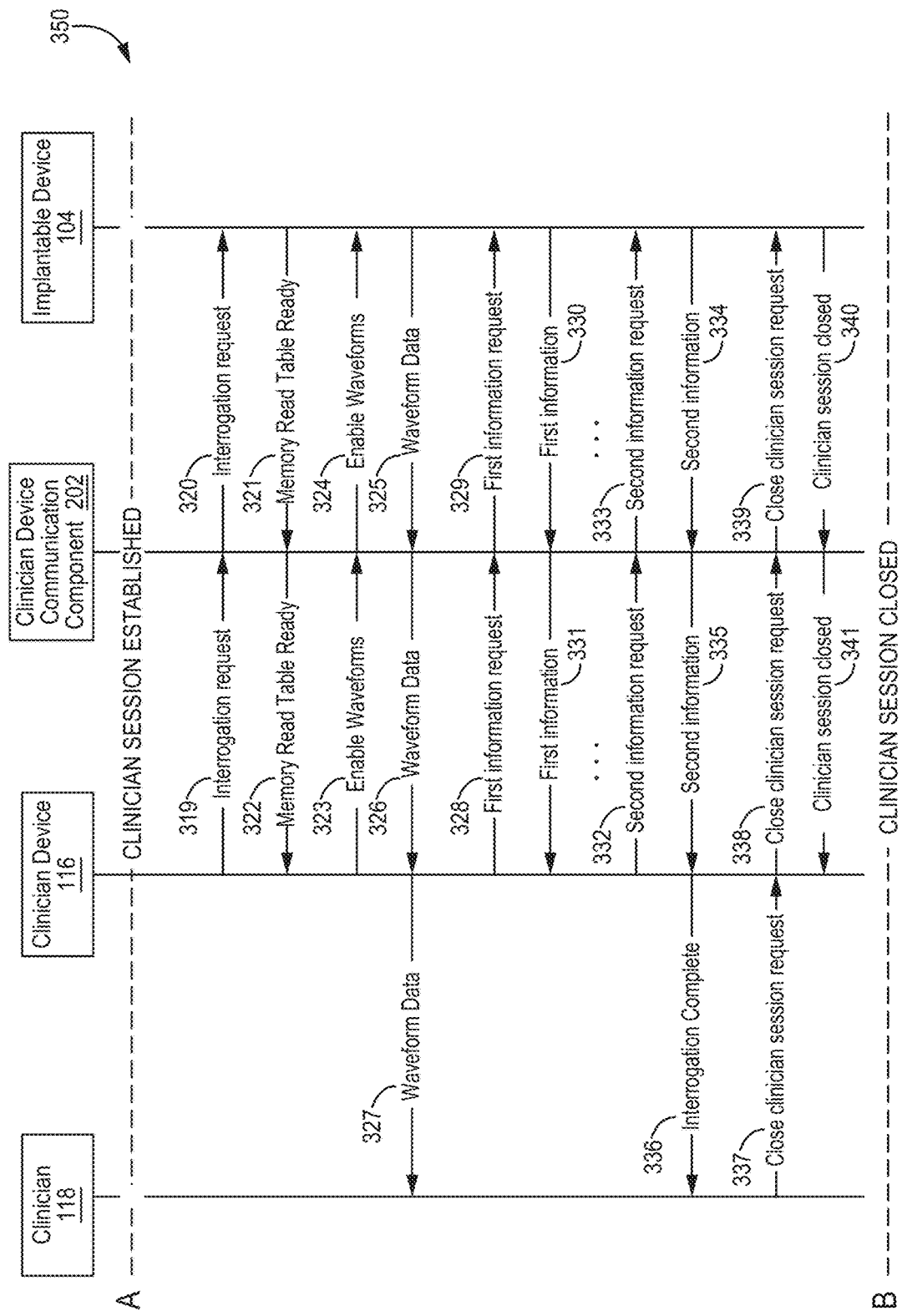
FIG. 3B illustrates a non-limiting signaling diagram of a method facilitating secure data communication in association with performance of a secure clinician telemetry session between an implantable device and a clinician device in accordance with one or more embodiments described herein.

FIG. 3B illustrates a non-limiting signaling diagram of a signaling method 350 facilitating secure data communication in association with performance of a secure clinician telemetry session between an implantable device (e.g., implantable device 104) and a clinician device (e.g., clinician device 116) in accordance with one or more embodiments described herein. Repetitive description of like elements employed in other embodiments described herein is omitted for sake of brevity.

With reference to FIGS. 1, 2A, 2B, 3A and 3B, signaling method 350 includes a flow of signaling commands or messages between the clinician 118, the clinician device 116, the clinician device communication component 202, and the implantable device 104 in association with performing an established clinician session in accordance with one or more embodiments described herein. In one or more implementations, signaling method 350 is a continuation of signaling method 300 after the clinician session is established between the implantable device 104 and the clinician device 116, as indicated by dashed line A in FIG. 3A.

At 319, the clinician device 116 can send an interrogation request to the clinician device communication component 202. The interrogation request can include a request for information from the implantable device 104. In some implementations, the interrogation request can include a request for defined information from the implantable device 104. In other implementations, the interrogation request can include a request for a digest or index of all information available on the implantable device 104. For exemplary purposes, signaling method 350 is described wherein the interrogation request includes a request for such a digest or index. According to this embodiment, at 320, the clinician device communication component 202 can generate and send the interrogation request to the implantable device 104 using the second telemetry communication protocol. In response to reception of the interrogation request, at 321, the implantable device 104 can respond by sending a memory read table message to the clinician device communication component 202. The memory read table message can include for example, a table of addresses and/or links to information provided on the implantable device 104 (e.g., in memory of the implantable device 104). At 322, the clinician device communication component 202 can forward the memory read table message to the clinician device 116.

In various embodiments, the memory read table can include information identifying the implantable device 104, can include waveform data, and can be capable of generating and providing the waveform data to the clinician device 116. In particular, in an embodiment in which the implantable device 104 is or includes an ICD, the ICD can capture electrical signals of the heart via one or more leads (e.g., leads 110a,b), referred to herein as "waveform data." The live waveform mode refers to an operating mode of the implantable device 104 wherein the implantable device 104 can transmit waveform data to the clinician device 116 in real-time. In this context, the term "real-time" can be within a defined amount of time after the waveform data is captured. The waveform data can be transmitted during a clinician session.

In the embodiment shown, the clinician device 116 can direct the implantable device 104 to activate the live waveform mode wherein the implantable device 104 generates and provides live (or real-time) waveform data captured by the implantable device 104 to the clinician device 116. For example, at 323, the clinician device 116 can send an enable waveform request to the clinician device communication component 202, which can format and send the enable waveform request to the implantable device 104 using the second telemetry communication protocol at 324. In response to reception of the enable waveform request, at 325, the implantable device 104 can send the waveform data to the clinician device communication component 202 in real-time as the waveform data is captured by the implantable device 104 using the second telemetry communication protocol. The clinician device communication component 202 can further provide the live waveform data to the clinician device 116 at 326. The live waveform data can be rendered to the clinician 118 via a display screen of the clinician device at 116 at 327.

In addition to waveform data, the memory read table can identify a variety of other types of information provided by the implantable device 104, such as information about the body 102 of the patient monitored by the implantable device 104, information regarding operating parameters of the implantable device 104, information regarding an amount of drug remaining in drug application reservoir of the implantable device 104, etc. For example, at 328, the clinician device 116 can send a first information request to the clinician device communication component 202, which can generate and send the first information request to the implantable device 104 using the second telemetry communication protocol at 329. The first information request can include a request for first specific information included in the memory read table, for example.

At 330, the implantable device 104 can respond with the first requested information using the second telemetry communication protocol. At 331, the first information can be received by the clinician device communication component 202 and can be forwarded by the clinician device communication component 202 to the clinician device 116. At 332, the clinician device 116 can send a second information request to the clinician device communication component 202, which can generate and send the second information request to the implantable device 104 using the second telemetry communication protocol at 333. The second information request can include a request for second specific information included in the memory read table. At 334, the implantable device 104 can respond with the second requested information using the second telemetry communication protocol. At 335, the second information can be received by the clinician device communication component 202 and forwarded by the clinician device communication component 202 to the clinician device 116.

Once the clinician device 116 has received all requested information, at 336, the clinician device 116 can provide an output for the clinician 118 (e.g., via a speaker and/or display screen of the clinician device 116) that indicates the interrogation is complete. If the clinician does not have any additional information to request from or provided to the implantable device, at 337, the clinician can provide input requesting to close the clinician session. At 338, the clinician device 116 can then provide the close clinician session request to the clinician device communication component 202, which can generate and provide the close clinician session request to the implantable device 104 using the second telemetry communication protocol at 339. At 340, the implantable device 104 can then close the clinician session and remove (or otherwise render expired), the clinician session security information from memory (e.g., the unique session identifier, the link key and the application key).

Once the security information is removed, the implantable device 104 can send a message to the clinician device communication component 202 using the second communication protocol informing the clinician device 116 that the clinician session has been closed. At 341, the clinician device communication component 202 can provide the clinician session closed message to the clinician device 116. At this time, the clinician session can be considered closed, as indicated by dashed line B.

It should be appreciated that the various types of communication performed in accordance with the clinician session described via signaling method 350 are merely exemplary. For example, the type of information communicated between the clinician device 116 and the implantable device 104 during an established clinician session can vary depending on the features and functionalities of the clinician device, the implantable device 104 and the purpose of the clinician session (as determined by the clinician 118).

In various embodiments, some or all communication signals or messages communicated between the clinician device 116, the clinician device communication component 202 and implantable device 104 during the clinician session can be encrypted with the link key, the application layer encryption key, or a combination of both the link and application layer encryption keys. In one or more embodiments, all data besides waveform data that is communicated between the clinician device 116, the clinician device communication component 202 and implantable device 104 during the clinician session are encrypted with both the link key and the application key. However, in some embodiments, waveform data may not be encrypted using the application key to facilitate the efficient transmission and reception of live data. In addition, at the close of the clinician session, if waveform mode by the implantable device 104 has been enabled, the implantable device 104 can automatically disable waveform mode and stop sending live waveform data using the second communication protocol.

Figure 4:
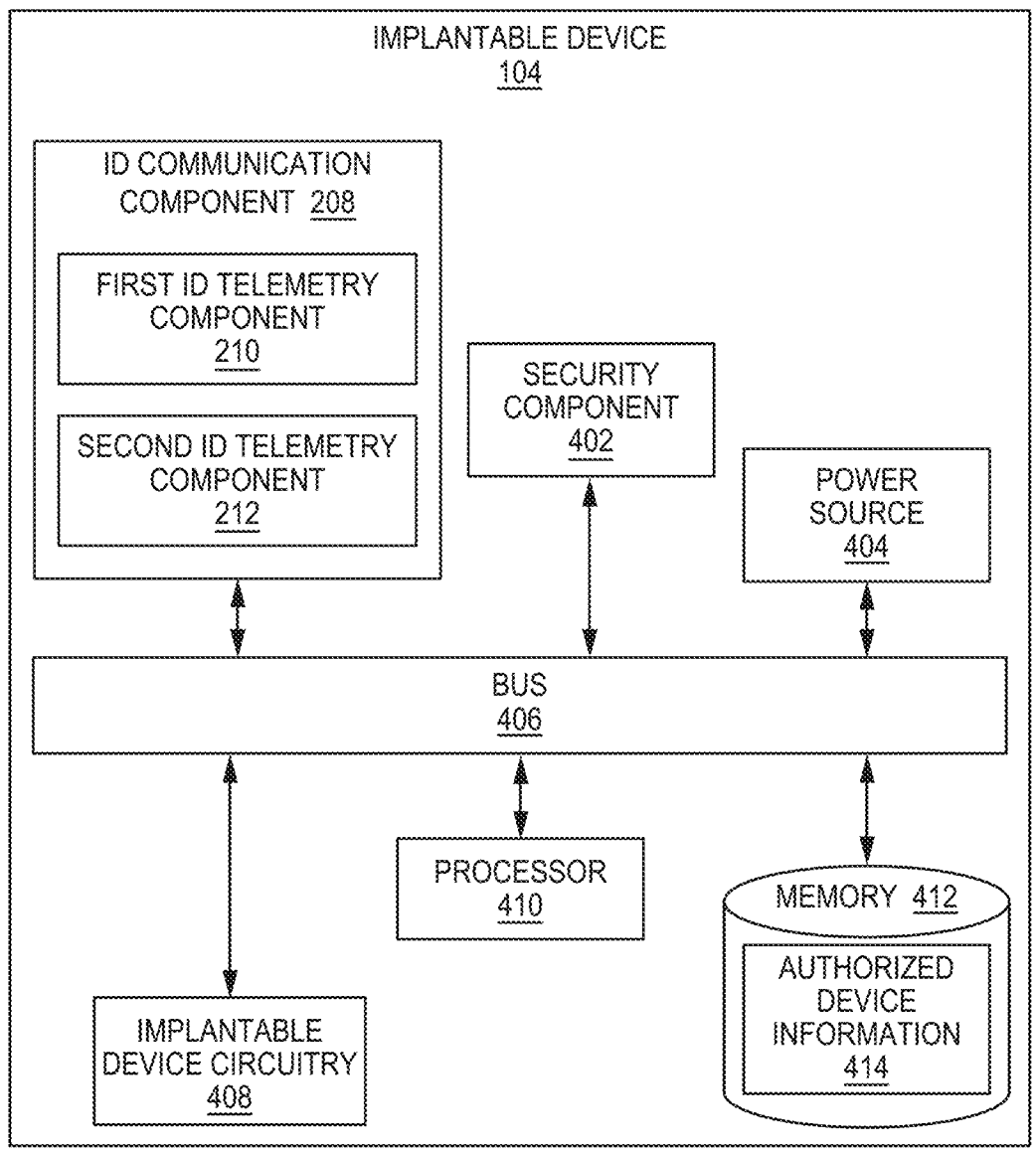
FIG. 4 illustrates a block diagram of an example, non-limiting implantable device in accordance with one or more embodiments described herein.

FIG. 4 illustrates a block diagram of an example, non-limiting implantable device (e.g., implantable device 104) in accordance with one or more embodiments described herein. The implantable device 104 includes implantable device communication component 208 and security component 402, a power source 404, and implantable device circuitry 408. The implantable device 104 can include memory 412 configured to store computer executable components and instructions and processor 410 to facilitate operation of the instructions (e.g., computer executable components and instructions) by the implantable device 104. The implantable device 104 can include a bus 406 that couples the various components of the implantable device 104, including, but not limited to, the implantable device communication component 208, the security component 402, the power source 404, the implantable device circuitry 408, the processor 410 and the memory 412. Repetitive description of like elements employed in other embodiments described herein is omitted for sake of brevity.

Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described.

With reference to FIGS. 1, 2, and 4, the security component 402 can be configured to facilitate performance of the subject security processes in association with establishing and performing a clinician telemetry session by the implantable device 104. In particular, the security component 402 can facilitate performance of the primary and secondary telemetry communication exchange, encoding and decoding of information during an established clinician session, re-establishing a lost clinician telemetry session, and ensuring the security information generated by the implantable device for a clinician session cannot be used at a later time after the clinician session is closed. For example, in some embodiments, in response to reception of a properly formatted telemetry clinician session initiation request via the first telemetry communication protocol and recognition of a clinician device identifier in the clinician session initiation request, the security component 402 can generate the some or all of the time-sensitive security information required to establish and conduct the clinician session using the second telemetry communication protocol (e.g., a unique session identifier and one or more unique session keys). In other embodiments, the security component 402 can receive some or all of the security information from the clinician device 116 with the clinician session initiation request.

In some implementations, the security component 402 can further store the clinician device identifier and the security information generated for the currently requested clinician session in memory 412 of the implantable device 104 (e.g., as authorized device information 414). The security component 402 can further authorize establishment of a clinician session based on reception of a properly formatted connection request via the second telemetry communication protocol (e.g., that includes the clinician device identifier and/or that is encrypted and thus able to be decrypted using one or more of the unique session keys). The security component 402 can further encrypt information for transmission by the implantable device and decrypt information received by the implantable device during the clinician session. In some implementations, the security component 402 can further remove the security information from memory 412 or otherwise render the security information unusable to establish another telemetry session in the future based on closing of the clinician telemetry session.

The implantable device circuitry 408 can include hardware, software or a combination of hardware and software employed to facilitate operation of the various components of the implantable device 104. For example, the implantable device circuitry 408 can include, but is not limited to: a pulse generator, capacitors, leads (e.g., leads 110a,b), electrodes (e.g., tip electrodes 112a,b and ring electrodes 114a,b), sensors, accelerometers, pumping mechanisms, reservoirs, implantable device communication component 208 hardware (e.g., antennas, transmitters, receivers, transceivers repeaters, etc.), a therapy output module, and the like. The implantable device circuitry 408 can facilitate various operations of the implantable device, including, but not limited to, medical related operations (e.g., sensing electrical signals of the heart, dispensing a drug, etc.), and telemetry communication mode operations of the implantable device (e.g., RF telemetry and non-RF telemetry such as induction).

Implantable device 104 can further include power source 404 to drive the operations of implantable device 104 and provide power to the various electrical components of the implantable device 104. In one or more embodiments, the power source 404 includes, but is not limited to, a battery, a capacitor, a charge pump, a mechanically derived power source (e.g., microelectromechanical systems (MEMs) device), or an induction component. The induction component can also be employed by the second implantable device telemetry component 212 to facilitate transmission and reception of induction-based telemetry signals.

Figure 5:
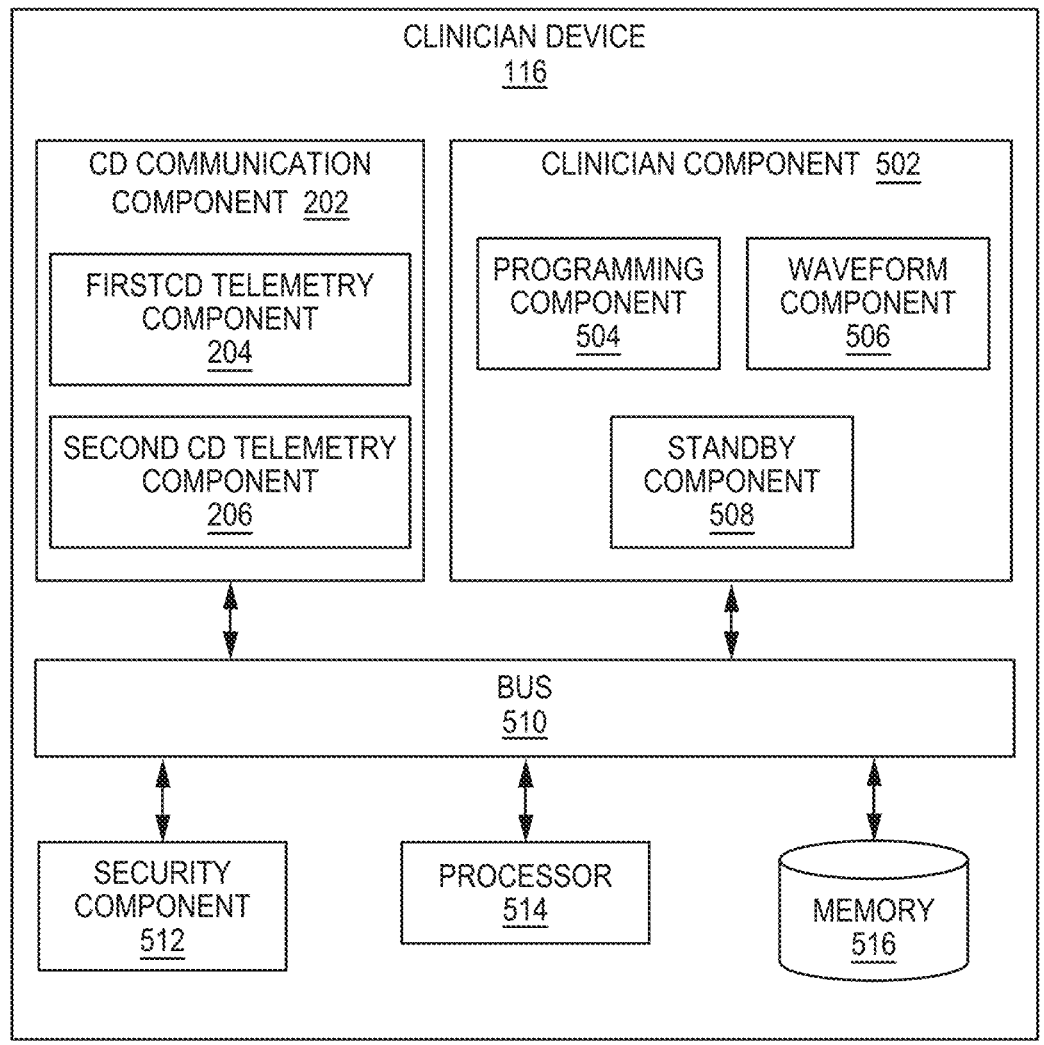
FIG. 5 illustrates a block diagram of an example, non-limiting clinician device in accordance with one or more embodiments described herein.

FIG. 5 illustrates a block diagram of an example, non-limiting clinician device (e.g., clinician device 116) in accordance with one or more embodiments described herein. The clinician device 116 can include any suitable computing device that can be operated by a clinician and configured to communicate with an implantable device (e.g., implantable device 104) using a first (e.g., induction-based) telemetry communication protocol and a second (e.g., BLE) telemetry communication protocol. For example, the clinician device 116 can include a smartphone, a tablet, a dedicated handheld device, a wearable device, or another suitable device. In some embodiments, the clinician device 116 can include an output and/or input device such as a display, a speaker, a microphone, a keypad, a touchscreen etc. In other embodiments, the clinician device 116 can be configured to communicate with another remote device to receive input and/or render output.

The clinician device 116 includes clinician device communication component 202, clinician component 502, and security component 512. The clinician device 116 can include memory 516 configured to store computer executable components and instructions and processor 514 to facilitate operation of the instructions (e.g., computer executable components and instructions) by the clinician device 116. The clinician device 116 can include a bus 510 that couples the various components of the clinician device 116, including, but not limited to, the clinician device communication component 202, clinician component 502, and security component 512, the processor 514 and the memory 516.

Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described.

With reference to FIGS. 1, 2, and 5, the security component 512 can facilitate establishing a trusted clinician telemetry session between the clinician device 116 and the implantable device 104. For example, the security component 512 can direct the first clinician device telemetry component 204 to generate and send a clinician session initiation request to the implantable device 104 using the first telemetry communication protocol (e.g., induction signal) and include a unique identifier for the clinician device 116 in the clinician session initiation request (e.g., an RFM address). The first clinician device telemetry component 204 can further receive a response signal to the remote clinician session initiation request from the implantable device 104 via the first telemetry communication protocol (e.g., another induction signal) and the security component 512 can extract the security information included in the response signal. In one or more implementations, the security information includes a unique session identifier and one or more session keys. The security component 512 can further store the security information in memory 516.

In some embodiments, the security component 512 can also include some or all of the security information in the clinician session initiation request. For example, the security component 512 can generate security information including the unique session identifier and/or the one or more session keys and include the security information in the clinician session initiation request. In some implementations, rather than generating the security information, the security component 512 can request and receive the security information from another device (e.g., a remote server device (not shown)). In another embodiment, the security component 512 can be configured to generate or receive the unique session identifier and include the unique session identifier in the clinician session initiation request along with a clinician device identifier. The implantable device 104 can further generate the one or more session keys based on reception of the clinician session initiation request. The implantable device 104 can provide the one or more session keys to the security component 512 using a response message transmitted via the first telemetry communication protocol.

The security component 512 can further identify advertisement data packets transmitted by the implantable device 104 based on inclusion and recognition of the unique session identifier in the advertisement data packets. The security component 512 can also direct the second clinician device telemetry component 206 to send a connection request to the implantable device and include the unique identifier for the clinician device in the connection request. The implantable device 104 can establish an authorized clinician telemetry session with the clinician device 116 based on reception of the connection request. After the remote clinician telemetry session is established, the second clinician device telemetry component 206 can employ the one or more session keys to encrypt and decrypt information communicated between the implantable device 104 and the clinician device 116.

The clinician device 116 includes clinician component 502 to facilitate conducting clinician telemetry session with the implantable device 104. For example, the clinician component 502 can facilitate requesting specific information from the implantable device and sending specific information to the implantable device 104. The clinician component 502 can include programming component 504, waveform component 506 and standby component 508. The programming component 504 can facilitate generating and sending programming commands to the implantable device 104. The waveform component 506 can facilitate activating and deactivating a waveform mode of the implantable device 104 and receiving live waveform data from the implantable device 104. The standby component 508 can facilitate requesting entry of and exit of the implantable device 104 to and from the standby mode.

FIGS. 6, 7, 8, 9 and 10 illustrate flow diagrams of example, non-limiting methods that facilitate telemetry data communication security between an implantable device and an external device in accordance with one or more embodiments described herein. While, for purposes of simplicity of explanation, the methodologies are shown and described as a series of acts, the disclosed subject matter is not limited by the order of acts, as some acts can occur in different orders and/or concurrently with other acts from that shown and described herein. For example, those skilled in the art will understand and appreciate that a methodology can alternatively be represented as a series of interrelated statuses or events, such as in a state diagram. Moreover, not all illustrated acts may be required to implement a methodology in accordance with the disclosed subject matter. Additionally, it is to be appreciated that the methodologies disclosed in this disclosure are capable of being stored on an article of manufacture to facilitate transporting and transferring such methodologies to computers or other computing devices. The following methods facilitate enhanced security associated with establishing and performing a telemetry session with the implantable device (e.g., implantable device 104) using an RF-based telemetry communication protocol (e.g., BLE) that enables rapid (and high power consuming) bi-directional telemetry communication with the implantable device 104 of data considered invasive or sensitive (e.g., programming data or waveform data associated with a remote clinician telemetry session).

Figure 6:
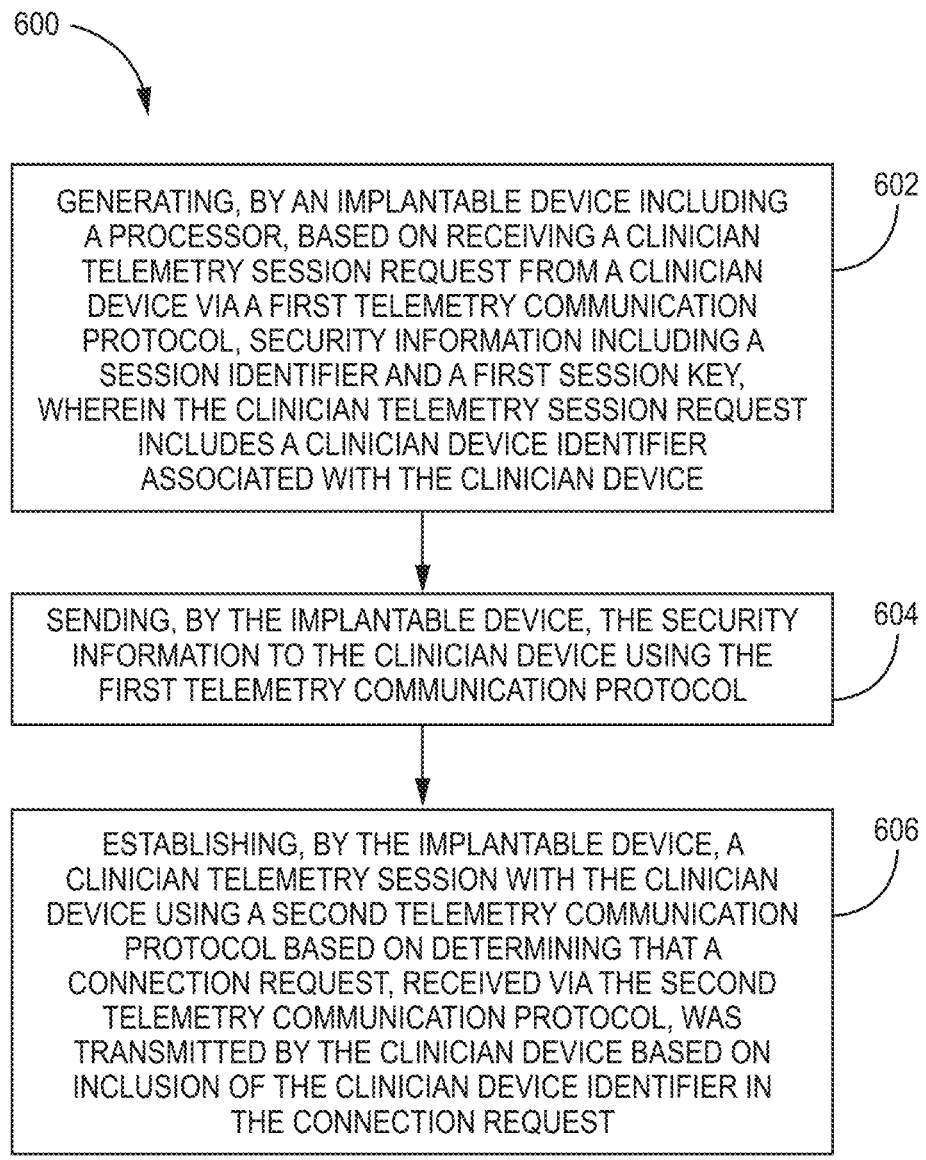
FIGS. 6, 7, 8, 9 and 10 illustrate flow diagrams of example, non-limiting methods that facilitate telemetry data communication security between an implantable device and an external device in accordance with one or more embodiments described herein.

Referring now to FIG. 6, shown is a flow diagram of an example method 600 configured to facilitate telemetry data communication security between an implantable device (e.g. implantable device 104) and an external device (e.g., clinician device 116) in accordance with one or more embodiments described herein. Repetitive description of like elements employed in other embodiments described herein is omitted for sake of brevity.

At 602, an implantable device including a processor (e.g., implantable device 104) can generate, based on receiving a clinician telemetry session request from a clinician device (e.g., clinician device 116) via a first telemetry communication protocol (e.g., an induction-based telemetry communication protocol), security information including a session identifier and a first session key, wherein the clinician telemetry session request includes a clinician session identifier associated with the clinician device. At 604, the implantable device can send the security information to the clinician device using the first telemetry communication protocol. At 606, the implantable device can establish a clinician telemetry session with the clinician device using a second telemetry communication protocol (e.g., BLE) based on determining that a connection request, received via the second telemetry communication protocol, was transmitted by the clinician device based on inclusion of the clinician device identifier in the connection request.

Figure 7:
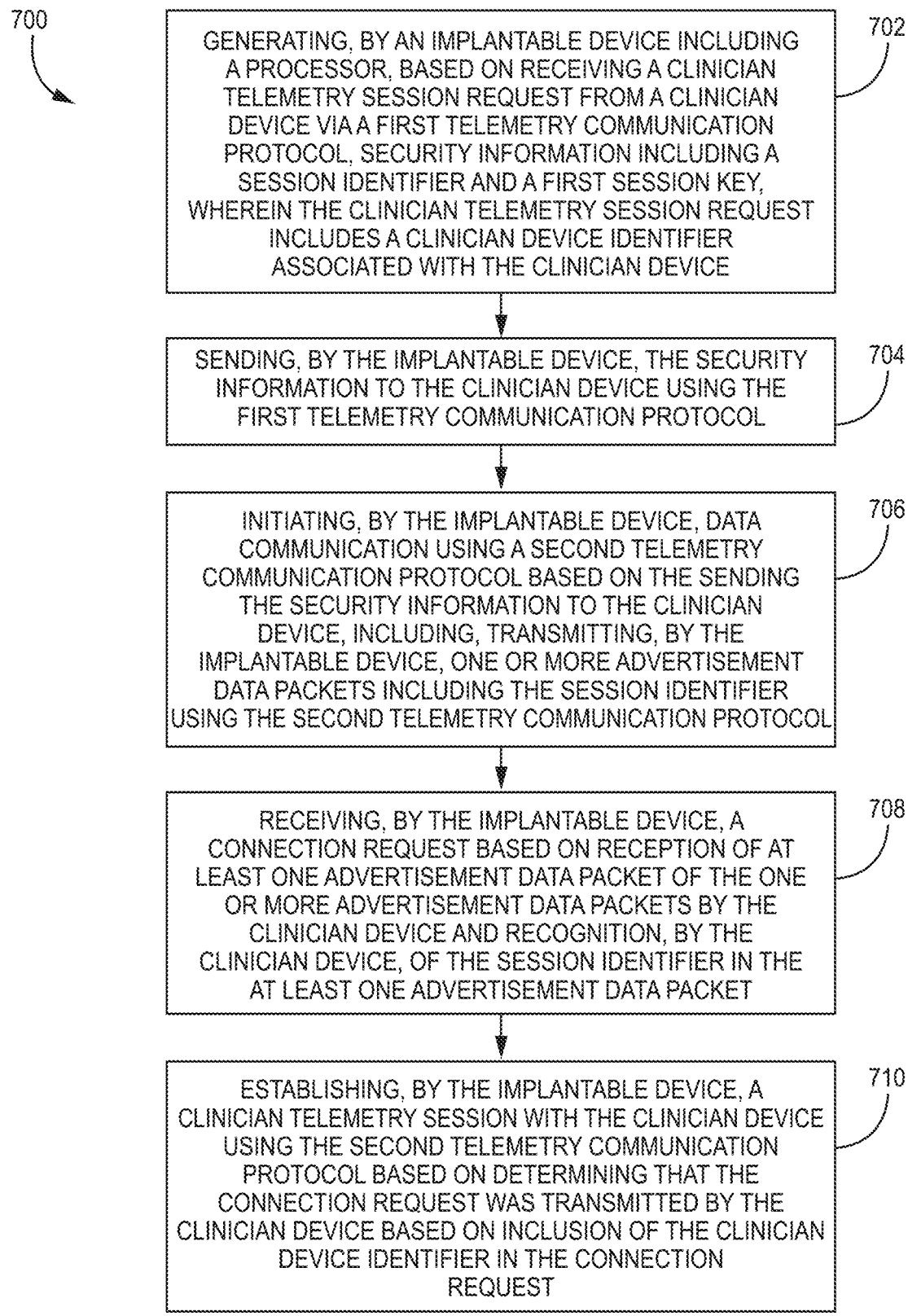

Referring now to FIG.7, shown is a flow diagram of another example method 700 configured to facilitate telemetry data communication security between an implantable (e.g. implantable device 104) and an external device (e.g., clinician device 116) in accordance with one or more embodiments described herein. Repetitive description of like elements employed in other embodiments described herein is omitted for sake of brevity.

At 702, an implantable device including a processor (e.g., implantable device 104) can generate, based on receiving a clinician telemetry session request from a clinician device (e.g., clinician device 116) via a first telemetry communication protocol (e.g., an induction-based telemetry communication protocol), security information including a session identifier and a first session key, wherein the clinician telemetry session request includes a clinician device identifier associated with the clinician device. At 704, the implantable device can send the security information to the clinician device using the first telemetry communication protocol. At 706, the implantable device can initiate data communication using a second telemetry communication protocol (e.g., BLE) based on the sending the security information to the clinician device, including, transmitting, by the implantable device, one or more advertisement data packets including the session identifier using the second telemetry communication protocol.

At 708, the implantable device receives a connection request based on reception of at least one advertisement data packet of the one or more advertisement data packets by the clinician device and recognition, by the clinician device, of the session identifier in the at least one advertisement data packet. At 710, the implantable device establishes a clinician telemetry session with the clinician device using the second telemetry communication protocol based on determining that the connection request was transmitted by the clinician device based on inclusion of the clinician device identifier in the connection request.

Figure 8:
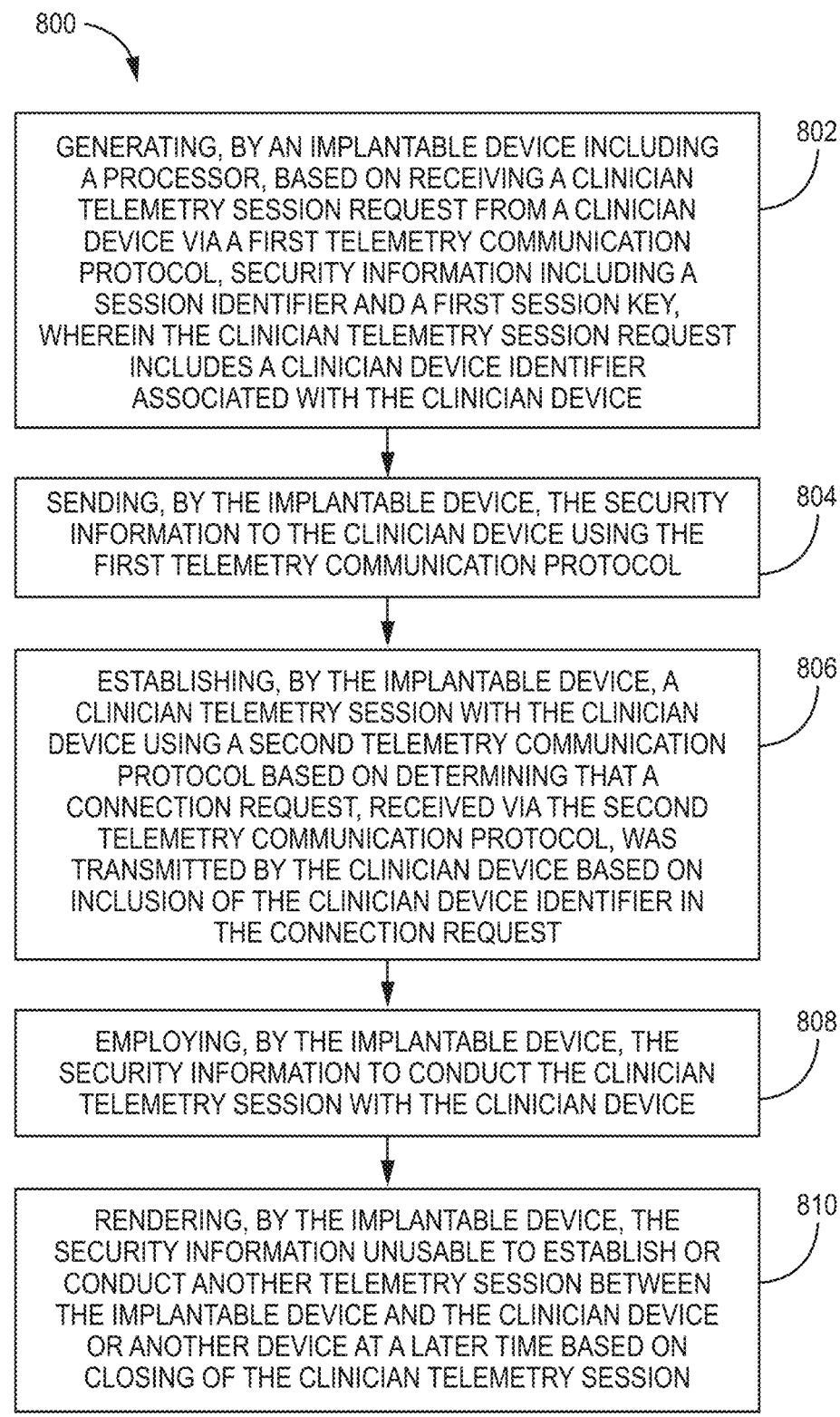

Referring now to FIG. 8, shown is a flow diagram of another example method 800 configured to facilitate telemetry data communication security between an implantable (e.g. implantable device 104) and an external device (e.g., clinician device 116) in accordance with one or more embodiments described herein. Repetitive description of like elements employed in other embodiments described herein is omitted for sake of brevity.

At 802, an implantable device including a processor (e.g., implantable device 104) can generate, based on receiving a clinician telemetry session request from a clinician device (e.g., clinician device 116) via a first telemetry communication protocol (e.g., an induction-based telemetry communication protocol), security information including a session identifier and a first session key, wherein the clinician telemetry session request includes a clinician device identifier associated with the clinician device. At 804, the implantable device can send the security information to the clinician device using the first telemetry communication protocol. At 806, the implantable device can establish a clinician telemetry session with the clinician device using a second telemetry communication protocol (e.g., BLE) based on determining that a connection request, received via the second telemetry communication protocol, was transmitted by the clinician device based on inclusion of the clinician device identifier in the connection request. At 808, the implantable device can employ the security information to conduct the clinician telemetry session with the clinician device. For example, the implantable device can encrypt and decrypt data communicated between the implantable device and the clinician device using the first session key. The implantable device can also include the session identifier in messages transmitted by the implantable device to the clinician device. At 810, the implantable device can render the security information unusable to establish or conduct another telemetry session between the implantable device and the clinician device or another device at a later time based on closing of the clinician telemetry session. For example, the implantable device can remove the security information from memory of the implantable device or render the security information expired (e.g., using the security component 402). Accordingly, in order for the clinician device or another clinician device to establish and conduct a new telemetry session with the implantable device, the clinician device or the other clinician device and the implantable device can establish and exchange new security information in association with a clinician session request.

Figure 9:
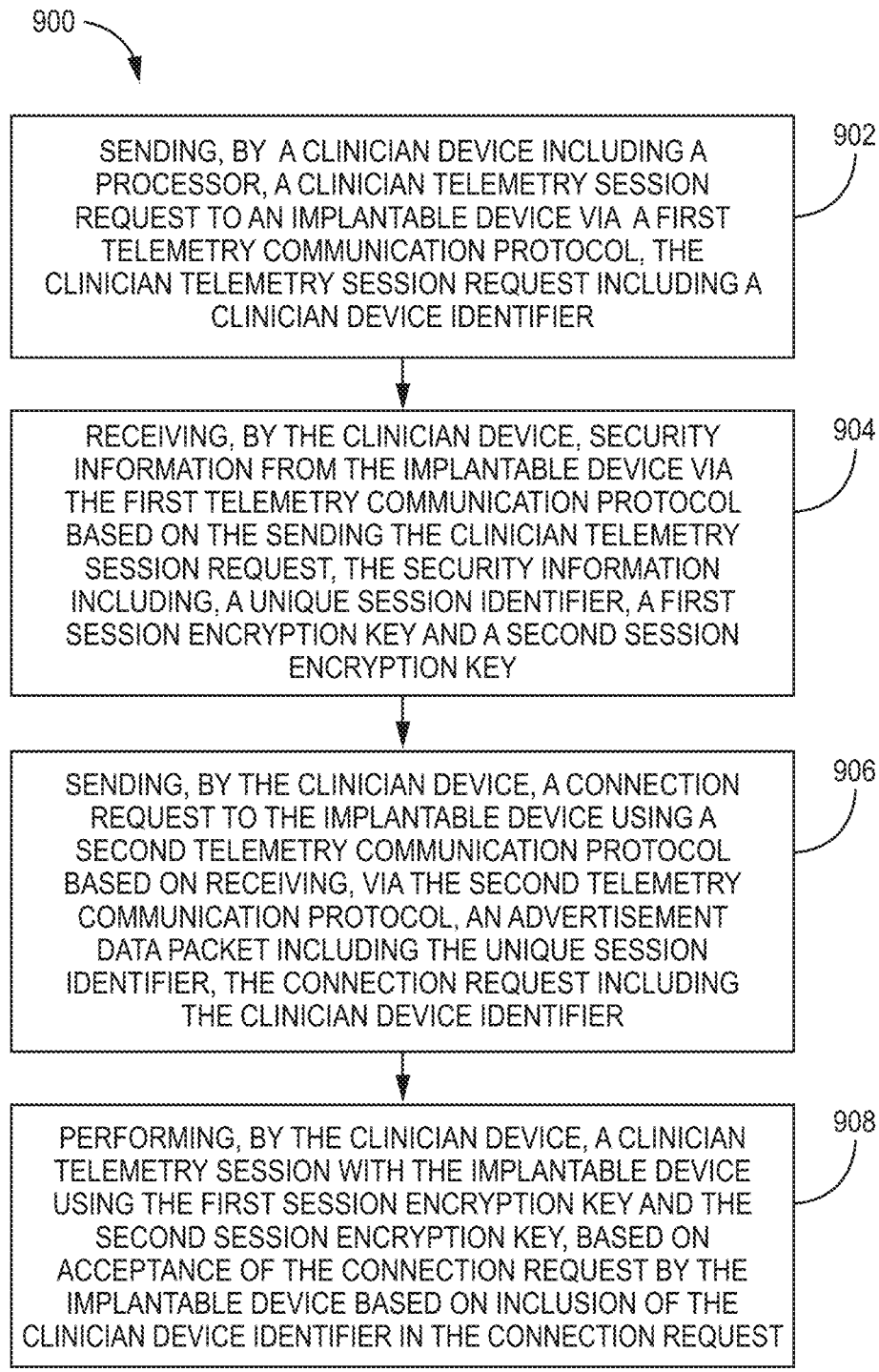

Referring now to FIG. 9, shown is a flow diagram of another example method 900 configured to facilitate telemetry data communication security between an implantable (e.g. implantable device 104) and an external device (e.g., clinician device 116) in accordance with one or more embodiments described herein. In one or more embodiments, a clinician device (e.g., clinician device 116) can employ a first telemetry communication component (e.g., first clinician device telemetry component 204), a second telemetry component (e.g., second clinician device telemetry component 206), and a security component (e.g., security component 512) to facilitate establishing and performing a clinician session with an implantable device (e.g., implantable device 104) in accordance with method 900. Repetitive description of like elements employed in other embodiments described herein is omitted for sake of brevity.

At 902, a clinician device including a processor (e.g., clinician device 116) can send a clinician telemetry session request to an implantable device via a first telemetry communication protocol (e.g., an induction-based protocol), the clinician telemetry session request including a clinician device identifier (e.g., an RFM address associated with the clinician device). At 904, the clinician device can receive security information from the implantable device via the first telemetry communication protocol based on the sending the clinician telemetry session request, the security information including, a unique session identifier (e.g., a unique UUID generated by the implantable device based on reception of the clinician telemetry session request), a first session encryption key (e.g., a link layer encryption key), and a second session encryption key (e.g., an application layer encryption key).

At 906, the clinician device can send a connection request to the implantable device using a second telemetry communication protocol based on receiving, via the second telemetry communication protocol, an advertisement data packet including the unique session identifier, the connection request including the clinician device identifier. At 908, the clinician device can perform a clinician telemetry session with the implantable device using the first session encryption key and the second session encryption key based on acceptance of the connection request by the implantable device based on inclusion of the clinician device identifier in the connection request. For example, the clinician device can use the first session encryption key and the second session encryption key to encrypt transmitted data transmitted by the clinician device to the implantable device (e.g., programming data, interrogation requests, etc.), or to decrypt received data received by the clinician device from the implantable device.

Figure 10:
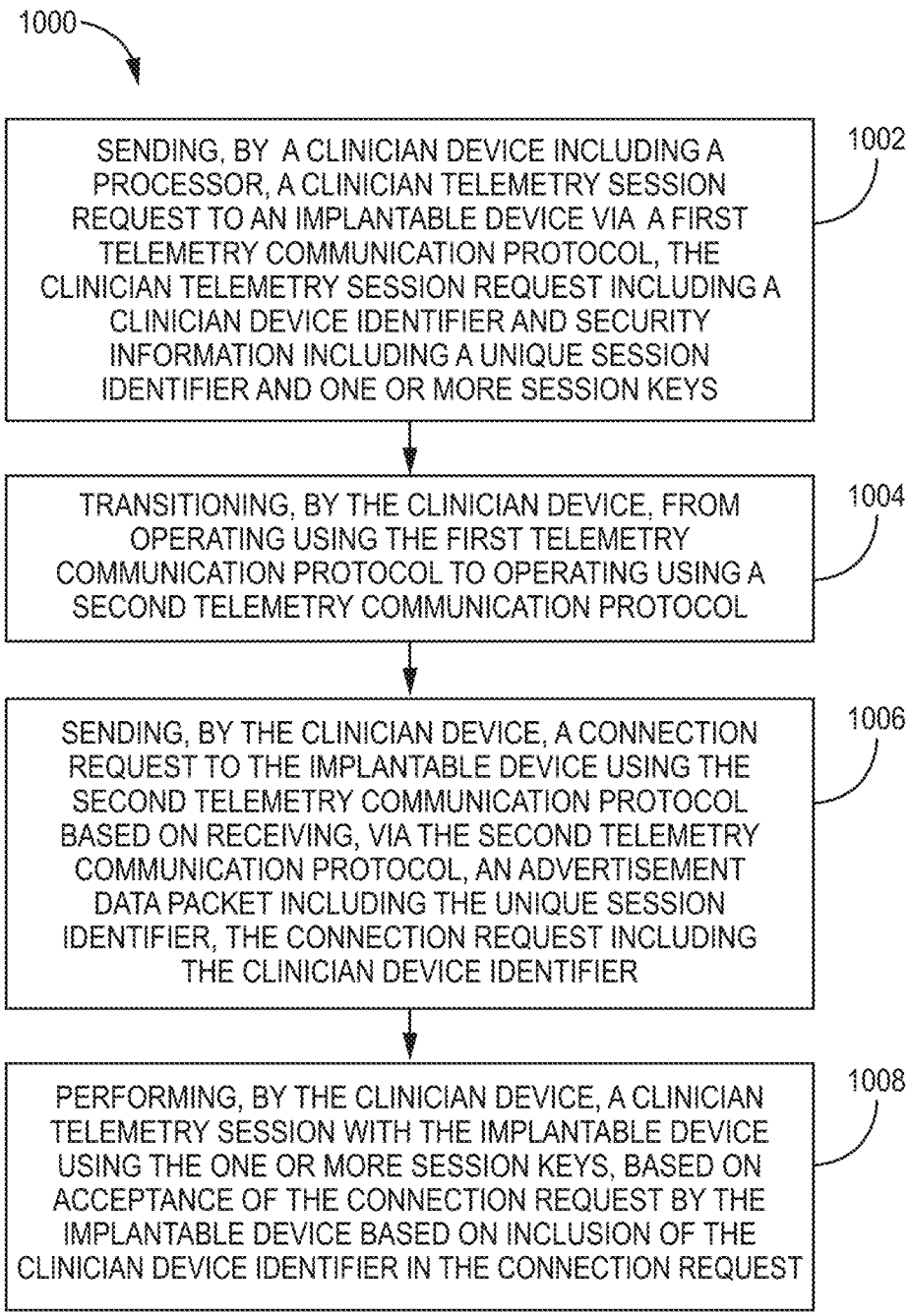

Referring now to FIG. 10, shown is a flow diagram of another example method 1000 configured to facilitate telemetry data communication security between an implantable device (e.g., implantable device 104) and an external device (e.g., clinician device 116) in accordance with one or more embodiments described herein. In one or more embodiments, a clinician device (e.g., clinician device 116) can employ a first telemetry communication component (e.g., first clinician device telemetry component 204), a second telemetry component (e.g., second clinician device telemetry component 206), and a security component (e.g., security component 512) to facilitate establishing and performing a clinician session with an implantable device (e.g., implantable device 104) in accordance with method 1000. Repetitive description of like elements employed in other embodiments described herein is omitted for sake of brevity.

At 1002, a clinician device including a processor (e.g., clinician device 116) can send a clinician telemetry session request to an implantable device via a first telemetry communication protocol (e.g., an induction-based protocol), the clinician telemetry session request including a clinician device identifier and security information including a unique session identifier (e.g., a unique UUID generated by the clinician device 116) and one or more session keys (e.g., a link layer encryption key and/or an application layer encryption key generated by the clinician device 116). At 1004, the clinician device can transition from operating using the first telemetry communication protocol to using a second telemetry communication protocol (e.g., BLE protocol). At 1006, the clinician device can send a connection request to the implantable device using the second telemetry communication protocol based on receiving, via the second telemetry communication protocol, an advertisement data packet including the unique session identifier. The connection request can include the clinician device identifier. At 1008, the clinician device can perform a clinician telemetry session with the implantable device using the one or more session keys based on acceptance of the connection request by the implantable device based on inclusion of the clinician device identifier in the connection request. For example, the clinician device can use the one or more session keys to encrypt transmitted data transmitted by the clinician device to the implantable device (e.g., programming data, interrogation requests, etc.) or to decrypt received data received by the clinician device from the implantable device.

Figure 11:
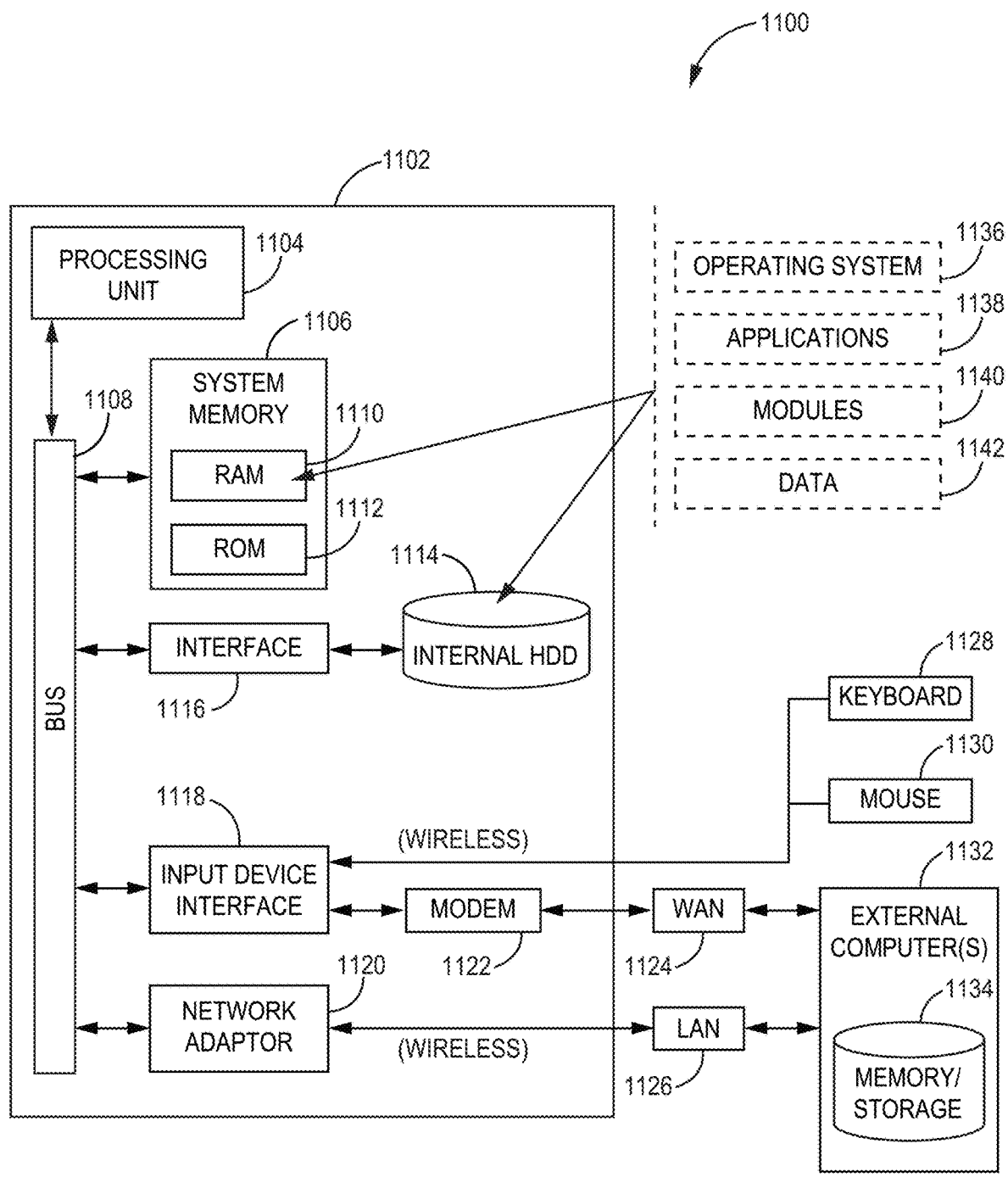
FIG. 11 illustrates a block diagram of an example, non-limiting computer operable to facilitate telemetry data communication security between an implantable device and an external device in accordance with one or more embodiments described herein.

FIG. 11 illustrates a block diagram of an example, non-limiting computer operable to facilitate managing telemetry communication modes of an implantable device in accordance with one or more embodiments described herein. For example, in some embodiments, the computer can be or be included within implantable device 104 and the clinician device 116. Repetitive description of like elements employed in other embodiments described herein is omitted for sake of brevity.

In order to provide additional context for one or more embodiments described herein, FIG. 11 and the following discussion are intended to provide a brief, general description of a suitable computing environment 1100 in which the one or more embodiments described herein can be implemented.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

Computing devices typically include a variety of media, which can include computer-readable storage media and/or communications media, which two terms are used herein differently from one another as follows. Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data or unstructured data. Tangible and/or non-transitory computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD) or other optical disk storage, magnetic cassettes, magnetic tape, magnetic disk storage, other magnetic storage devices and/or other media that can be used to store desired information. Computer-readable storage media can be accessed by one or more local or remote computing devices, e.g., via access requests, queries or other data retrieval protocols, for a variety of operations with respect to the information stored by the medium.

In this regard, the term "tangible" herein as applied to storage, memory, computer-readable media or computer-readable storage media, is to be understood to exclude only propagating intangible signals per se as a modifier and does not relinquish coverage of all standard storage, memory, computer-readable media or computer-readable storage media that are not only propagating intangible signals per se.

In this regard, the term "non-transitory" herein as applied to storage, memory, computer-readable media or computer-readable storage media, is to be understood to exclude only propagating transitory signals per se as a modifier and does not relinquish coverage of all standard storage, memory, computer-readable media or computer-readable storage media that are not only propagating transitory signals per se.

Communications media typically embody computer-readable instructions, data structures, program modules or other structured or unstructured data in a data signal such as a modulated data signal, e.g., a channel wave or other transport mechanism, and includes any information delivery or transport media. The term "modulated data signal" or signals refers to a signal that has one or more of the data signal's characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 11, example environment 1110 that can be employed to implement one or more embodiments of the embodiments described herein includes computer 1112. Computer 1112 includes processing unit 1114, system memory 1116 and system bus 1118. System bus 1118 couples system components including, but not limited to, system memory 1116 to processing unit 1114. Processing unit 1104 can be any of various commercially available processors. Dual microprocessors and other multiprocessor architectures can also be employed as processing unit 1104.

System bus 1108 can be any of several types of bus structure that can further interconnect to a memory bus (with or without a memory controller), a peripheral bus, and a local bus using any of a variety of commercially available bus architectures. System memory 1106 includes RAM 1110 and ROM 1112. A basic input/output system (BIOS) can be stored in a non-volatile memory such as ROM, erasable programmable read only memory (EPROM), EEPROM, which BIOS contains the basic routines that help to transfer information between elements within computer 1102, such as during startup. RAM 1110 can also include a high-speed RAM such as static RAM for caching data.

Computer 1102 further includes internal hard disk drive (HDD) 1114 (e g , Enhanced Integrated Drive Electronics (EIDE), Serial Advanced Technology Attachment (SATA)). HDD 1114 can be connected to system bus 1108 by hard disk drive interface 1116. The drives and their associated computer-readable storage media provide nonvolatile storage of data, data structures, computer-executable instructions, and so forth. For computer 1102, the drives and storage media accommodate the storage of any data in a suitable digital format.

A number of program modules can be stored in the drives and RAM 1110, including operating system 1136, one or more application programs 1138, other program modules 1140 and program data 1142. All or portions of the operating system, applications, modules, and/or data can also be cached in RAM 1110. The systems and methods described herein can be implemented utilizing various commercially available operating systems or combinations of operating systems.

A mobile device can enter commands and information into computer 1102 through one or more wireless input devices, e.g., wireless keyboard 1128 and a pointing device, such as wireless mouse 1130. Other input devices (not shown) can include a smart phone, tablet, laptop, wand, wearable device or the like. These and other input devices are often connected to the processing unit 1104 through input device interface 1118 that can be coupled to system bus 1108, but can be connected by other interfaces, such as a parallel port, an IEEE serial port, a game port and/or a universal serial bus (USB) port.

Computer 1102 can operate in a networked environment using logical connections via wired and/or wireless communications to one or more remote computers, such as remote computer(s) 1132. Remote computer(s) 1132 can be a workstation, a server computer, a router, a personal computer, portable computer, microprocessor-based entertainment appliance, a peer device or other common network node, and typically includes many or all of the elements described relative to computer 1102, although, for purposes of brevity, only memory/storage device 1134 is illustrated. The logical connections depicted include wired/wireless connectivity to a local area network (LAN) 1126 and/or larger networks, e.g., WAN 1124, as well as smaller PANs involving a few devices (e.g., at least two). LAN and WAN networking environments are commonplace in the home, offices (e.g., medical facility offices, hospital offices) and companies, and facilitate enterprise-wide computer networks, such as intranets, all of which can connect to a global communications network (e.g., the Internet).

When used in a LAN networking environment, computer 1102 can be connected to local network through a wired and/or wireless communication network interface or adapter 1120. Adapter 1120 can facilitate wired or wireless communication to LAN 1126, which can also include a wireless access point (AP) connected to the LAN 1126 for communicating with adapter 1120.

When used in a WAN networking environment, computer 1102 can include modem 1122 or can be connected to a communications server on WAN 1124 or has other apparatus for establishing communications over WAN 1124, such as by way of the Internet. Modem 1122, which can be internal or external and a wired or wireless device, can be connected to system bus 1108 via input device interface 1118. In a networked environment, program modules depicted relative to computer 1102 or portions thereof, can be stored in a remote memory/storage device. It will be appreciated that the network connections shown are example and other apparatus of establishing a communications link between the computers can be used.

Computer 1102 can be operable to communicate with any wireless devices or entities operatively disposed in wireless communication via any number of protocols, including, but not limited to, NFC, Wi-Fi and/or BLUETOOTH® wireless protocols. Thus, the communication can be a defined structure as with a conventional network or simply an ad hoc communication between at least two devices.

NFC can allow point-to-point connection to an NFC-enabled device in the NFC field of an IMD within the home or at any location. NFC technology can be facilitated using an NFC-enabled smart phone, tablet or other device that can be brought within 3-4 centimeters of an implanted NFC component. NFC typically provides a maximum data rate of 424 kilobits per second (Kbps), although data rates can range from 6.67 Kbps to 828 Kbps. NFC typically operates at the frequency of 10.56 megahertz (MHz). NFC technology communication is typically over a range not exceeding 0.2 meters (m) and setup time can be less than 0.1 seconds. Low power (e.g., 10 milliamperes (mAs)) reading of data can be performed by an NFC device.

Wi-Fi can allow connection to the Internet from a couch at home, a bed in a hotel room or a conference room at work, without wires. Wi-Fi is a wireless technology similar to that used in a cell phone that enables such devices, e.g., computers, to send and receive data indoors and out. Wi-Fi networks use radio technologies called IEEE 802.11 (a, b, g, n, etc.) to provide secure, reliable, fast wireless connectivity. A Wi-Fi network can be used to connect computers to each other, to the Internet, and to wired networks (which can use IEEE 802.3 or Ethernet). Wi-Fi networks operate in the unlicensed 2.4 and 5 GHz radio bands, at an 11 Mbps (802.11a) or 54 Mbps (802.11b) data rate, for example or with products that contain both bands (dual band), so the networks can provide real-world performance similar to the basic 10BaseT wired Ethernet networks used in many offices.

The embodiments of devices described herein can employ artificial intelligence (AI) to facilitate automating one or more features described herein. The embodiments (e.g., in connection with automatically identifying acquired cell sites that provide a maximum value/benefit after addition to an existing communication network) can employ various AI-based schemes for carrying out one or more embodiments thereof. Moreover, the classifier can be employed to determine a ranking or priority of each cell site of an acquired network. A classifier is a function that maps an input attribute vector, x=(x1, x2, x3, x4, xn), to a confidence that the input belongs to a class, that is, f(x)=confidence(class). Such classification can employ a probabilistic and/or statistical-based analysis (e.g., factoring into the analysis utilities and costs) to prognose or infer an action that a mobile device desires to be automatically performed. A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated, one or more of the embodiments can employ classifiers that are explicitly trained (e.g., via a generic training data) as well as implicitly trained (e.g., via observing mobile device behavior, operator preferences, historical information, receiving extrinsic information). For example, SVMs can be configured via a learning or training phase within a classifier constructor and feature selection module. Thus, the classifier(s) can be used to automatically learn and perform a number of functions, including but not limited to determining according to a defined criteria which of the acquired cell sites will benefit a maximum number of subscribers and/or which of the acquired cell sites will add minimum value to the existing communication network coverage, etc.

As employed herein, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components or any combination thereof designed to perform the functions described herein. Processors can exploit nano-scale architectures such as, but not limited to, molecular and quantum-dot based transistors, switches and gates, in order to optimize space usage or enhance performance of mobile device equipment. A processor can also be implemented as a combination of computing processing units.

Memory disclosed herein can include volatile memory or nonvolatile memory or can include both volatile and nonvolatile memory. By way of illustration, and not limitation, nonvolatile memory can include ROM, programmable ROM (PROM), electrically programmable ROM (EPROM), electrically erasable PROM (EEPROM) or flash memory. Volatile memory can include RAM, which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The memory (e.g., data storages, databases) of the embodiments is intended to include, without being limited to, these and any other suitable types of memory.

As used herein, terms such as "data storage," "database," and substantially any other information storage component relevant to operation and functionality of a component, refer to "memory components," or entities embodied in a "memory" or components including the memory. It will be appreciated that the memory components or computer-readable storage media, described herein can be either volatile memory or nonvolatile memory or can include both volatile and nonvolatile memory.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word "example" or "exemplary" is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application should generally be construed to mean "one or more" unless specified otherwise or clear from context to be directed to a singular form. The terms "first," "second," "third," and so forth, as used in the claims and description, unless otherwise clear by context, is for clarity only and doesn't necessarily indicate or imply any order in time.

What has been described above includes mere examples of one or more embodiments. It is, of course, not possible to describe every conceivable combination of components or methodologies for purposes of describing these examples, but one of ordinary skill in the art can recognize that many further combinations and permutations of the present embodiments are possible. Accordingly, the embodiments disclosed and/or claimed herein are intended to embrace all such alterations, modifications and variations that fall within the spirit and scope of the detailed description and the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An implantable device, comprising:
    a housing configured to be implanted at least partially within a patient;
    a memory, coupled to the housing, that stores executable components;
    circuitry, coupled to the housing, and configured to at least one of obtain sensed physiological data associated with the patient or deliver a therapy to the patient; and
    a processor, coupled to the housing, and the processor is configured to:
        generate security information based on reception of a clinician telemetry session request from a clinician device via a first telemetry communication protocol, the security information comprising a session identifier, a first session key, and a second session key, and the clinician telemetry session request comprising a clinician device identifier associated with the clinician device;
        activate telemetry communication by the implantable device via a second telemetry communication protocol based on sending the security information to the clinician device using the first telemetry communication protocol;
        establish a clinician telemetry session with the clinician device using the second telemetry communication protocol based on determining that a connection request, received via the second telemetry communication protocol, was transmitted by the clinician device based on inclusion of the clinician device identifier in the connection request;
        encrypt first transmitted data transmitted by the implantable device using the first session key in association with performance of the clinician telemetry session with the clinician device; and
        encrypt second transmitted data transmitted by the implantable device using the second session key in association with the performance of the clinician telemetry session with the clinician device, wherein the first transmitted data represents a first data type, and wherein the second transmitted data represents a second data type different from the first data type.

2. The implantable device of claim 1, wherein the first telemetry communication protocol comprises a proprietary telemetry communication protocol and the second telemetry communication protocol comprises a non-proprietary telemetry communication protocol.

3. The implantable device of claim 1, wherein the first telemetry communication protocol is associated with first wireless data communication over a first distance and the second telemetry communication protocol is associated with second wireless data communication over a second distance longer than the first distance.

4. The implantable device of claim 1, wherein the first telemetry communication protocol comprises an induction-based telemetry communication protocol and the second telemetry communication protocol comprises a Bluetooth low energy based telemetry communication protocol.

5. The implantable device of claim 1, wherein the processor is further configured to:
transmit one or more advertisement data packets comprising the session identifier using the second telemetry communication protocol in association with activation of the telemetry communication by the implantable device via the second telemetry communication protocol.

6. The implantable device of claim 5, wherein the processor is further configured to:
receive the connection request based on reception of at least one advertisement data packet of the one or more advertisement data packets by the clinician device and recognition, by the clinician device, of the session identifier in the at least one advertisement data packet.

7. The implantable device of claim 1, wherein the processor is further configured to:
decrypt first received data received by the implantable device using the first session key in association with performance of the clinician telemetry session with the clinician device.

8. The implantable device of claim 7, wherein the processor is further configured to:
decrypt second received data received by the implantable device using the second session key in association with the performance of the clinician telemetry session with the clinician device.

9. The implantable device of claim 7, wherein the processor is further configured to:
decrypt the first received data using the first session key and the second session key in association with the performance of the clinician telemetry session with the clinician device.

10. The implantable device of claim 1, wherein after establishment of the clinician telemetry session, the processor is further configured to:
communicate data with the clinician device using the security information in association with performance of the clinician telemetry session with the clinician device, and wherein the security component is further configured to:
render the security information unusable to establish or perform another telemetry session including the implantable device after a closing of the clinician telemetry session.

11. The implantable device of claim 1, wherein the processor is further configured to:
render the security information unusable to establish or perform another telemetry session including the implantable device after a failure of the implantable device to re-establish the clinician telemetry session using the security information within a defined period of time after loss of the clinician telemetry session.

12. The implantable device of claim 1, wherein the processor is further configured to:
inhibit the telemetry communication,
during establishment of the clinician telemetry session between the implantable device and the clinician device or
during the clinician telemetry session between the implantable device and the clinician device.

13. The implantable device of claim 1, wherein the security information comprises first security information and wherein the processor is further configured to:
receive second security information from a remote server device for establishing a monitoring telemetry session with a monitor; and
employ the second security information to establish a trusted relationship with the monitor and store information associating a monitoring device identifier for the monitor in the memory, wherein the processor is further configured to:
establish the monitoring telemetry session with the monitor using the second telemetry communication protocol based on determining that the monitoring session request, received via the second telemetry communication protocol, was transmitted by the monitor based on inclusion of the monitoring device identifier in the monitoring session request.

14. The implantable device of claim 13, wherein the implantable device is further configured to communicate a first type of information with the clinician device during the clinician telemetry session and a second type of information with the monitor during the monitoring telemetry session, wherein the first type of information is classified as having a first level of sensitivity and the second type of information is classified as having a second level of sensitivity and wherein the first level of sensitivity is greater than the second level of sensitivity.

15. The implantable device of claim 13, wherein the implantable device is configured to perform one-way and two-way communications with the clinician device during the clinician telemetry session, and wherein the implantable device is configured to perform one-way and forgo two-way communications with the monitoring device during the monitoring telemetry session.

16. The implantable device of claim 13, wherein the implantable device is configured to receive programming information from the clinician device during the clinician telemetry session and forgo receipt of the programming information from the monitor during the monitoring telemetry session.

17. A method comprising:
generating, by a processor of an implantable device, based on receiving a clinician telemetry session request from a clinician device via a first telemetry communication protocol, security information comprising a session identifier, a first session key, and a second session key, wherein the clinician telemetry session request comprises a clinician device identifier associated with the clinician device;
sending, by the processor, the security information to the clinician device using the first telemetry communication protocol;
establishing, by the processor, a clinician telemetry session with the clinician device using a second telemetry communication protocol based on determining that a connection request, received via the second telemetry communication protocol, was transmitted by the clinician device based on inclusion of the clinician device identifier in the connection request; and
performing, by the processor, the clinician telemetry session, wherein the performing comprises:
encrypting first transmitted data transmitted by the implantable device using the first session key in association with performance of the clinician telemetry session with the clinician device; and
encrypting second transmitted data transmitted by the implantable device using the second session key in association with the performance of the clinician telemetry session with the clinician device, wherein the first transmitted data represents a first data type, and wherein the second transmitted data represents a second data type different from the first data type.

18. The method of claim 17, wherein the first telemetry communication protocol comprises an induction-based telemetry communication protocol and the second telemetry communication protocol comprises a Bluetooth Low Energy-based telemetry communication protocol.

19. The method of claim 17, further comprising:
initiating, by the processor, data communication using the second telemetry communication protocol based on the sending the security information to the clinician device, wherein the initiating comprises transmitting, by the implantable device, one or more advertisement data packets comprising the session identifier using the second telemetry communication protocol.

20. The method of claim 19, further comprising:
receiving, by the processor, the connection request based on reception of at least one advertisement data packet of the one or more advertisement data packets by the clinician device and recognition, by the clinician device, of the session identifier in the at least one advertisement data packet.

21. The method of claim 17,
wherein the performing further comprises decrypting first received data by the implantable device using the first session key.

22. The method of claim 21, wherein the performing further comprises decrypting second received data by the implantable device using the second session key.

23. The method of claim 17, further comprising:
employing, by the processor, the security information to conduct the clinician telemetry session with the clinician device; and
rendering, by the processor, the security information unusable to establish another telemetry session including the implantable device after a closing of the clinician telemetry session.

24. A system, comprising:
a clinician device configured to perform telemetry communication with other devices using a first telemetry communication protocol and a second telemetry communication protocol; and
an implantable device comprising:
a first telemetry component configured to perform the first telemetry communication protocol;
a second telemetry component configured to perform the second telemetry communication protocol; and
a security software module configured to:
generate security information based on reception of a clinician telemetry session request from the clinician device via the first telemetry communication component, the security information comprising a session identifier and one or more session keys, wherein the one or more session keys include a first session key and a second session key, and the clinician telemetry session request comprising a clinician device identifier associated with the clinician device, wherein the second telemetry component is configured to establish a clinician telemetry session with the clinician device using the second telemetry communication protocol based on determining that a connection request, received via the second telemetry communication protocol, was transmitted by the clinician device based on recognition of the clinician device identifier in the connection request;
encrypt first transmitted data transmitted by the implantable device using the first session key in association with performance of the clinician telemetry session with the clinician device; and
encrypt second transmitted data transmitted by the implantable device using the second session key in association with the performance of the clinician telemetry session with the clinician device, wherein the first transmitted data represents a first data type, and wherein the second transmitted data represents a second data type different from the first data type.

25. The system of claim 24, wherein the first telemetry communication protocol facilitates first wireless data communication over a first distance and the second telemetry communication protocol facilitates second wireless data communication over a second distance that is greater than the first distance.

26. The system of claim 24, wherein prior to establishing the clinician telemetry session with the clinician device, the implantable device is further configured to:
transmit the security information to the clinician device using the first telemetry component;
transmit one or more advertisement data packets comprising the session identifier using the second telemetry component; and
receive the connection request using the second telemetry component based on reception of at least one advertisement data packet of the one or more advertisement data packets by the clinician device and recognition, by the clinician device, of the session identifier in the at least one advertisement data packet.

27. The system of claim 24, wherein the implantable device is further configured to:
render, using the security software module, the security information unusable to establish or perform another telemetry session including the implantable device after a failure of the implantable device and the clinician device to re-establish the clinician telemetry session using the security information within a defined period of time after loss of the clinician telemetry session.

28. The system of claim 24, wherein the implantable device is further configured to:
forgo, using the security software module, the telemetry communication during establishment of the clinician telemetry session between the implantable device and the clinician device.

29. A non-transitory computer readable medium comprising computer executable instructions that, in response to execution, cause at least one processor of an implantable device to perform operations, comprising:
generating, based on receiving a clinician telemetry session request from a clinician device via a first telemetry communication protocol, security information comprising a session identifier and one or more session keys, wherein the one or more session keys include a first session key and a second session key, and wherein the clinician telemetry session request comprises a clinician device identifier associated with the clinician device;

transmitting the security information to the clinician device using the first telemetry communication protocol;

transmitting one or more advertisement data packets comprising the session identifier and using a second telemetry communication protocol;

establishing a clinician telemetry session with the clinician device using the second telemetry communication protocol based on reception, by the clinician device, of at least one advertisement data packet of the one or more advertisement data packets;

encrypting first transmitted data transmitted by the implantable device using the first session key in association with performance of the clinician telemetry session with the clinician device; and encrypting second transmitted data transmitted by the implantable device using the second session key in association with the performance of the clinician telemetry session with the clinician device, wherein the first transmitted data represents a first data type, and wherein the second transmitted data represents a second data type different from the first data type.

30. The non-transitory computer readable medium of claim 29, wherein the operations further comprise:
receiving a connection request from the clinician device via the second telemetry communication protocol.

31. The non-transitory computer readable medium of claim 30, wherein the establishing comprises establishing the clinician telemetry session based on inclusion of the clinician device identifier in the connection request.

32. A method comprising:
sending, by a processor of a clinician device, a clinician telemetry session request to an implantable device via a first telemetry communication protocol, the clinician telemetry session request comprising a clinician device identifier and security information including a unique session identifier and one or more session keys, wherein the one or more session keys include a first session key and a second session key;

transitioning, by the processor, from operating using the first telemetry communication protocol to operating using a second telemetry communication protocol based on the sending the clinician telemetry session request;

sending, by the processor, a connection request to the implantable device using the second telemetry communication protocol based on receiving, via the second telemetry communication protocol, an advertisement data packet including the unique session identifier, wherein the connection request includes the clinician device identifier;

performing, by the processor, a clinician telemetry session with the implantable device using the one or more session keys based on acceptance of the connection request by the implantable device based on inclusion of the clinician device identifier in the connection request;

encrypting first transmitted data transmitted by the implantable device using the first session key in association with performance of the clinician telemetry session with the clinician device;

encrypting second transmitted data transmitted by the implantable device using the second session key in association with the performance of the clinician telemetry session with the clinician device, wherein the first transmitted data represents a first data type, and wherein the second transmitted data represents a second data type different from the first data type; and requesting, by the clinician device, entry of and exit of the implantable device to and from a standby mode.

* * * * *